US007761462B2

(12) United States Patent
Bjornson et al.

(10) Patent No.: US 7,761,462 B2
(45) Date of Patent: *Jul. 20, 2010

(54) SEARCHING QUERIES USING DATABASE PARTITIONING

(76) Inventors: Robert D. Bjornson, 6 Tyler Ave., Branford, CT (US) 06405; Nicholas J. Carriero, 827 Still Hill Rd., Hamden, CT (US) 06518; Andrew H. Sherman, 1 Crestview Dr., North Haven, CT (US) 06473; Stephen B. Weston, 89 Carleton St., Hamden, CT (US) 06517; James E. Wing, 265 College St., Apt. 3D, New Haven, CT (US) 06510

( * ) Notice: Subject to any disclaimer, the term of this patent is extended or adjusted under 35 U.S.C. 154(b) by 0 days.

This patent is subject to a terminal disclaimer.

(21) Appl. No.: 11/969,878

(22) Filed: Jan. 4, 2008

(65) Prior Publication Data
US 2008/0104041 A1    May 1, 2008

Related U.S. Application Data

(63) Continuation of application No. 10/700,071, filed on Nov. 3, 2003, now Pat. No. 7,333,980, which is a continuation of application No. 09/814,056, filed on Mar. 22, 2001, now Pat. No. 6,691,109.

(51) Int. Cl.
*G06F 17/00* (2006.01)
*G06F 7/00* (2006.01)
*G06F 9/46* (2006.01)
(52) U.S. Cl. ........................ 707/764; 718/106
(58) Field of Classification Search ................. None
See application file for complete search history.

(56) References Cited

U.S. PATENT DOCUMENTS

| 5,555,201 | A | 9/1996 | Dangelo et al. |
| 5,625,823 | A | 4/1997 | Debenedictis et al. |
| 5,701,256 | A | 12/1997 | Marr et al. |
| 5,828,894 | A | 10/1998 | Wilkinson et al. |
| 5,873,052 | A | 2/1999 | Sharaf |
| 5,884,303 | A | 3/1999 | Brown |
| 5,999,729 | A | 12/1999 | Tabloski et al. |
| 6,009,422 | A | 12/1999 | Ciccarelli |
| 6,088,044 | A | 7/2000 | Kwok et al. |

(Continued)

OTHER PUBLICATIONS

Chakravarthy "Divide and conquer: a basis for augmenting a conventional query optimizer with multiple query processing capabilities", IEEE 1991, pp. 482-490.

(Continued)

*Primary Examiner*—Uyen T. Le
(74) *Attorney, Agent, or Firm*—Stolowitz Ford Cowger LLP

(57) ABSTRACT

Embodiments include partitioning queries into subsets of queries and at least one database into subdatabases, designating searching tasks by associating each of the subsets of queries with one or more of the subdatabases, and assigning at least one searching task to at least one computer of a group of computers operating in parallel. Embodiments further describe designating two or more subtasks as related tasks on a virtual shared memory bulletin board, executing the at least one searching task using the at least one computer of the group of computers operating in parallel, and generating a search result responsive to the executing.

39 Claims, 14 Drawing Sheets

U.S. PATENT DOCUMENTS

| | | | |
|---|---|---|---|
| 6,112,225 | A | 8/2000 | Kraft et al. |
| 6,289,334 | B1 | 9/2001 | Reiner |
| 6,523,030 | B1 | 2/2003 | Horowitz |
| 6,691,109 | B2 | 2/2004 | Bjornson |
| 6,850,925 | B2 | 2/2005 | Chaudhuri |
| 6,985,898 | B1 * | 1/2006 | Ripley et al. ............ 707/5 |
| 7,017,147 | B2 | 3/2006 | Hayase et al. |
| 7,137,116 | B2 | 11/2006 | Parkes |
| 7,184,967 | B1 | 2/2007 | Mital et al. |
| 7,231,390 | B2 | 6/2007 | Blair |
| 7,240,328 | B2 | 7/2007 | Beckett et al. |
| 2001/0053957 | A1 | 12/2001 | Blair et al. |
| 2002/0199034 | A1 | 12/2002 | Beckett et al. |
| 2003/0055813 | A1 | 3/2003 | Chaudhuri et al. |
| 2005/0066304 | A1 | 3/2005 | Tattrie et al. |

OTHER PUBLICATIONS

Jiang et al, "Dynamic parallel query processing for distributed objects", Database and Expert Systems Applications, 1998. Proceedings. 9th international workgroup on, Aug. 26-28, 1998, pp. 699-704.

Salazar et al, "On an efficient parallelization of exhaustive sequence comparison algorithms on message passing architectures", Oxford University Press, vol. 10. No. 5, 1994, pp. 509-511.

Yap et al, "Parallel computation in biological sequence analysis", IEEE Transactions on Parallel and Distributed Systems, vol. 9, No. 3, Mar. 1998, pp. 283-294.

Gao et al, "Multithreaded implementation of a biomolecular sequence alignment algorithm-software/ information technology", IEEE 2000, pp. 494-498.

Wang et al, "Parallel R-tree search algorithm on DSVM", Database System for advanced applications, 1999. Proceedings, 6th international conference on, Apr. 19-21, 1999, pp. 237-244.

Yona et al "A unified sequence-structure classification of protein sequences: combining sequence and structure in a map of the protein space", ACM 2000, pp. 308-317.

Kosky et al "Facilitating transformations in a human genome project database", ACM 1994, pp. 423-432.* . BTG [now Blackstone Computing] Product Overview, 4 pp. no date.

BTG [now Blackstone Computing] Product Overview, 4 pp. no. date. . Scientific Computing Associates Inc., (1995) Paradise Product Overview, 2 pp.

Paradise: User's Guide & Reference Manual, Verison 6.2, Scientific Computing Associates (Apr. 2000) pp. 1-1 to 1-11; 4-1 to 4-11.

"SGI Bioinformatics Performance Report," Silicon Graphics, Inc., 10 pp. (Summer 2000).

Camp, "High-Throughput BLAST," Silicon Graphics, Inc., 15 pp. (Sep. 1998).

Harvey et al. "The Effectiveness of Task-Level Parallelism for High-Level Vision", ACM 1990, pp. 156-167.

Scientific Computing Associates Inc., (1995) Paradise Product Overview, 2 pp.

Davidson et al., "Facilitating Transformations in a Human Genome Project Database," ACM, p. 423 (1994).

* cited by examiner

SEARCHING QUERIES USING DATABASE PARTITIONING

CROSS-REFERENCE TO RELATED APPLICATIONS

This application is a continuation of U.S. application Ser. No. 10/700,071 filed Nov. 3, 2003, now issued as U.S. Pat. No. 7,333,980, which is a continuation of U.S. application Ser. No. 09/814,056 filed Mar. 22, 2001, now issued as U.S. Pat. No. 6,691,109. We incorporate the '071 application and the '109 patent herein by reference.

FIELD OF THE INVENTION

The invention relates to a method for searching multiple query sequences against one or more sequence databases. More specifically, the invention relates to a computer-implemented method and apparatus that provide high-performance, high-speed, remotely accessible sequence comparison searches.

BACKGROUND OF THE INVENTION

Sequence similarity is an observable quantity that may be expressed as, for example, a percentage. Comparison of newly identified sequences against known sequences often provides clues about the function of the sequences. If the sequence is a protein sequence, the sequence comparison may also provide clues as to the three-dimensional structure adopted by the protein sequence. Sequence similarity may also lead to inferences on the evolutionary relatedness, or the homology, of the sequences.

Current sequence databases are already immense and have continued to grow at an exponential rate. For example, the human genome project and other large scale nucleotide sequencing objectives have resulted in a large amount of sequence information available in both private and public databases. Sequence similarity searching is not simply used to compare a single sequence against the sequences in a single database, but is also used to compare or screen large numbers of new sequences against multiple databases. Moreover, sequence alignment and database searches are performed tens of thousands of times per day around the world. Therefore, the ability to quickly and precisely compare new sequence data against such sequence databases is becoming more and more important.

There are many different methods for comparing sequences. Some methods, such as those based on the analysis of transformational grammars (cf. Durbin, et al., Biological Sequence Analysis, Cambridge University Press (1998), Chapter 9), compare sequences by comparing the properties of the mathematical algorithms that may be used to generate the sequences in question. However, most common methods involve the use of sequence alignment at some point in the comparison process. Sequence alignment provides an explicit mapping between the residues of two or more sequences. When only two sequences are compared, the process is called pairwise alignment, but there are also methods of constructing multiple alignments that involve aligning more than two sequences.

The production of a sequence alignment result may be generically divided into two separate problems. The first problem is the alignment of the query sequence with the sequences in the databases being searched. The second problem is ranking or scoring of the aligned sequences. The results of the sequence alignment search are then reported as a ranked hit list followed by a series of individual sequence alignments, plus various scores and statistics.

There are various programs and algorithms available for performing database sequence similarity searching. For a basic discussion of bioinformatics and sequence similarity searching, see BIOINFORMATICS: A Practical Guide to the Analysis of Genes and Proteins, Baxevanis and Ouellette eds., Wiley-Interscience (1998) and Biological Sequence Analysis: Probabilistic Models of Proteins and Nucleic Acids, Durbin et al., Cambridge University Press (1998). One of the first used algorithms for performing sequence alignment searching was incorporated into the FASTA program. (Lipman and Pearson, "Rapid and sensitive protein similarity searches," Science, Vol. 227, PP. 1435-1441 (1985); Pearson and Lipman, "Improved tools for biological sequence comparison," Proc. Natl. Acad. Sci., Vol. 85, pp. 2444-2448 (1988)). The FASTA program performs optimized searches for local alignments using a substitution matrix. In order to improve the speed of the search, the program uses an observed pattern or small matches, termed "word" hits, to identify potential matches before performing the more time-consuming optimization search.

A popular algorithm for sequence similarity searching is the BLAST (Basic Local Alignment Search Tool) algorithm, which is employed in programs such as blastp, blastn, blastx, tblastn, and tblastx. (Altschul et al., "Local alignment statistics," Methods Enzymol., Vol. 266, pp. 460-480 (1996); Altschul et al., "Gapped BLAST and PSI-BLAST: A new generation of protein database search programs," Nucl. Acids Res., Vol. 25, pp. 3389-3402 (1997); Karlin et al., "Methods for assessing the statistical significance of molecular sequence features by using general scoring schemes," Proc. Natl. Acad. Sci., Vol. 87, pp. 2264-2268 (1990); Karlin et al., "Applications and statistics for multiple high-scoring segments in molecular sequences," Proc. Natl. Acad. Sci., Vol. 90, pp. 5873-5877 (1993)). The approach used by the BLAST program is to first identify segments, with or without gaps, that are similar in a query sequence and a database sequence, then to evaluate the statistical significance of all such matches that are identified, and finally to summarize only those matches that satisfy a preselected threshold of significance.

The blastp program compares an amino acid query sequence against a protein sequence database, while the blastn program compares a nucleotide query sequence against a nucleotide sequence database. The blastx program compares the six-frame conceptual translation products of a nucleotide query sequence (both strands) against a protein sequence database. A protein query sequence is compared against a nucleotide sequence database dynamically translated in all six reading frames (both strands) by the tblastn program, and tblastx compares the six-frame translations of a nucleotide query sequence against the six-frame translations of a nucleotide sequence database. The program blastall, one of the implementations of BLAST, can be used to perform all five flavors of the BLAST comparison.

The BLAST program can be downloaded from the NCBI and run locally as a full executable. It can be used to run BLAST searches against private local databases or downloaded copies of the NCBI databases. The 1.4 and later versions of BLAST are capable of being run in parallel using shared memory multiprocessors. (N. Camp, "High-Throughput BLAST," Silicon Graphics, Inc., September 1988, www.sgi.com/chembio/resources/pap-ers/HTBlast/HT_Whitepaper.html)

Silicon Graphics, Inc. ("SGI") has developed an alternative parallel system for running multiple BLAST searches. (N. Camp, "High-Throughput BLAST," Silicon Graphics, Inc., September 1988, www.sgi.com/chembio/resources/papers/ HTBlast/HT_Whitepaper.html). The system consists of a modified BLAST executable and a driver, and is called High-Throughput BLAST. ("HT BLAST"). HT BLAST allows multiple sequences to be compared against multiple databases by only a single invocation of code. The output of HT BLAST is a summary of the High Scoring Pair information generated during the search. Through a single invocation of code, HT BLAST saves on startup overhead through the reuse of data structures and elimination of the need to remap the databases. HT-BLAST also removes all parallel constructs from BLAST, allowing for increased single-processor speed. Parallelism has then been relocated to the driver which distributes blocks of sequences to multiple processors running HT BLAST. HT BLAST uses a dynamically scheduled loop to maintain load balance. As the independent tasks are blocks of sequences compared to multiple databases, the parallel grain-size can be much greater than it is for unmodified BLAST. Thus, scaling to large numbers of processors is accomplished even for short sequences and small databases.

HT BLAST, however, is run on a single multiprocessor mainframe. The method and apparatus of the instant invention allows a sequence similarity searching program, such as the BLAST executable, to be run on multiple, networked, heterogeneous machines. Moreover, HT-BLAST does not allow for dividing up collections of databases both by treating individual databases separately and by partitioning the individual databases. The method and apparatus of the instant invention do not require a shared disk architecture, whereas HT-BLAST assumes shared database storage and requires memory mapping. Finally, the method and apparatus of the instant invention manage multiple BLAST job requests through its queuing system.

The Blackstone Technology Group has developed a parallel processing system that allows for BLAST processing on a compute farm. ("SmartBlast™—Version 1.0," Blackstone Technology Group, http://www.computefarm.com/compute/ SmartBlast2.pdf (2001)). Compute farms are large groups of servers that merge computing power into a single resource that is mainly used for long-running and memory-intensive applications, such as those that handle vast amounts of genetic information. The system, SmartBlast™ distributes previously created segments of BLAST reference datasets to servers in the compute farm, based on demand. The segments are created using a proprietary data segmentation tool, Smart-Cache™ ("SmartCache.™.—Version 2.0," Blackstone Technology Group, http://www.computefarm.com/compute/ SmartCach-e2.pdf). Results are then collected, merged, and sorted by high scoring pair and presented in a single document.

The method and apparatus of the instant invention, as noted above, may be run on a wider class of machines/operating systems, including Windows and Macintosh, whereas the SmartBlast™ backend system only runs in a UNIX/Linux environment. In addition, in contrast to the apparatus and method disclosed herein, SmartBlast™ does not appear to divide up the input sequences. Finally, the apparatus and method of the instant invention allow for automatic partitioning of the databases during the search process, as well as in advance, based on the capabilities of the machines used for searching.

SUMMARY OF THE INVENTION

The invention relates to a computer-implemented method and apparatus for searching a plurality of query sequences against at least one sequence database containing a plurality of sequence records. The method comprises:

a. partitioning the plurality of query sequences into a set of smaller subsets of query sequences;

b. partitioning the at least one sequence database into a set of smaller subdatabases:

c. designating searching tasks to be performed by associating each of said subsets of query sequences with one or more of said subdatabases, assigning each searching task to one of a group of computers operating in parallel, wherein each member of the group of computers operating in parallel has at least one searching task assigned thereto, and executing at least some d. collecting search results from the executed searching tasks and generating a unified sequence search result in accordance with the collected search results.

Also disclosed is an apparatus for performing the above method, wherein the apparatus comprises:

a: means for partitioning the plurality of query sequences into a set of smaller subsets of query sequences;

b. means for partitioning the at least one sequence database into a set of smaller subdatabases;

c. means for designating searching tasks to be performed by associating each of said subsets of query sequences with one or more of said subdatabases:

d. means for assigning each searching task to one of a group of computers operating in parallel, wherein each member of the group of computers operating in parallel has at least one searching task assigned thereto;

e. means for executing at least some of the assigned searching tasks using the group of computers operating in parallel;

f. means for collecting search results from the executed searching tasks; and g. means for generating a unified sequence search result in accordance with the collected search results.

The invention also relates to the above method and apparatus, wherein the partitioning of the query sequences and the partitioning of the sequence database is done by each member of the group of computers operating in parallel. In addition, the method may also be performed wherein the partitioning of the query sequences and the partitioning of the sequence database is based on the processing capacity of each member of the group of computers operating in parallel, and each member of the group of computers operating in parallel may assign to itself which searching tasks it will perform. Each of the group of computers operating in parallel may perform one, two, or more searching tasks during the execution of the search, and each member may assign to itself another task once it finishes a searching task. The process may be reiterated, until all of the searching tasks are performed.

Each of the group of computers operating in parallel may be the same or different, and each of the group may have the same or different operating systems. Moreover, if one of the computers operating in parallel should fail, the correctness and/or precision of the search results will not be affected.

One or more of the sequence databases against which the query sequence is being compared may be derived from the databases maintained by the National Center for Biotechnology Information (NCBI). The plurality of query sequences are searched against one or more sequence databases, and each of the sequence databases may or may not be split into a set of smaller databases. The sequence databases may be searched using any desired algorithm, such as the BLAST algorithm. The unified sequence search result may be a sequence alignment. If the unified sequence search result is a sequence alignment, a raw score may be reported as part of the result. In addition, an e-score may also be reported as part of the search result, and the e-score may be normalized for each database searched as part of the generation of the unified search result. Moreover, the unified search result may be reported as a unified relevance ranked result list based on the normalized e-score.

The search results of each individual task may be collected by a single computer or by two or more computers of the group of computers operating in parallel. The unified search result may then be generated by interleaving the search results from the executed searching tasks on the basis of raw scores generated during the executed searching tasks. The method and the apparatus of the invention allow for superlinear speedup in the production of the unified search result, based on total time required to execute all searching tasks and produce the unified search result, which is equal to the duration of the period starting when the entire searching task is placed on a list of searching tasks accessible to all of the one or more computers operating in parallel and ending when the unified result for the entire searching task is placed on a list of results and a signal to exit has been sent to all of the computers operating in parallel. Superlinear speedup occurs when an increase in the number of computers operating in parallel causes a greater than pro rata reduction in the total time, as when the time required using four computers operating in parallel is less than one-half of the time required with two computers operating in parallel.

BRIEF DESCRIPTION OF THE DRAWINGS

FIG. 3A illustrates a graphical representation of an entire task searching 3 sequences against 2 databases.

FIG. 3Q illustrates a graphical representation of when Task 1.B.'s Buddy Task 1.A is READY, Processor 2 merges result for Task 1.B with result for Buddy Task 1.A., thereby computing result for Parent Task 1 (Box E). This completes the computation, since Task 1 is the Entire Task and has no Buddy Task.

DETAILED DESCRIPTION OF THE INVENTION

I. Definitions

Figure 1:
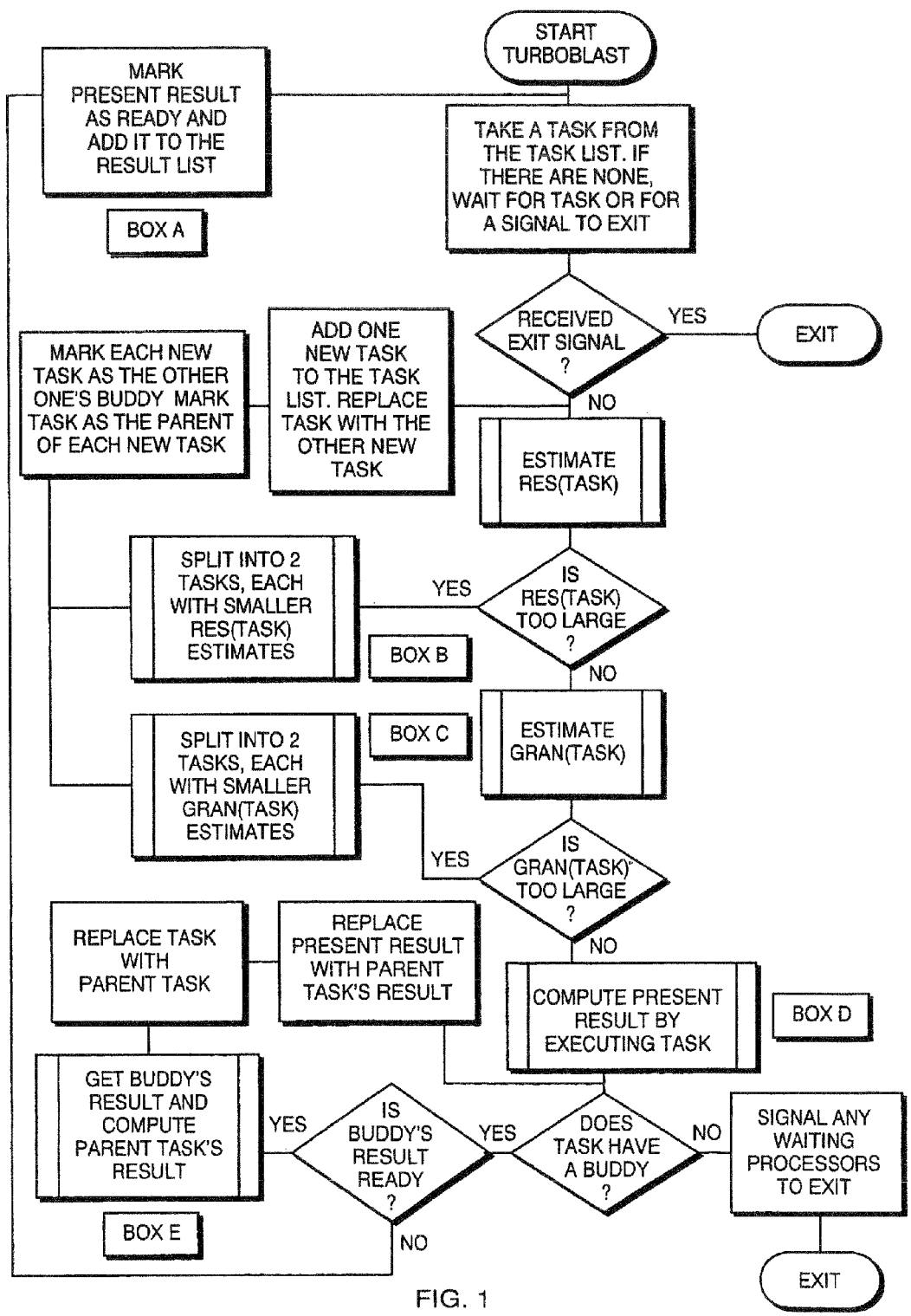
FIG. 1 is a flow chart depicting an overview of the sequence comparison method of the invention.

Virtual Shared Memory (VSM) allows applications to share objects and process data across distributed networks, such as local area networks. Commercially available programs, such as PARADISE™ for the JAVA™ platform, using the VSM concept, provide one or more network "bulletin boards," coordinate the processing of devices and components on a network, and facilitate their communication. Other programs that provide such network bulletin boards are well known in the art. A bulletin board may be used to store data or computer instructions, including descriptions of tasks to be executed or objects in a computer language such as JAVA. Any of the computers operating in parallel may access a VSM bulletin board by performing various operations, such as placing data on the bulletin board, examining data on the bulletin board, updating data on the bulletin board, or removing information from the bulletin board.

For example, in the instant method, a VSM bulletin board may be used to store descriptions of searching tasks and results of computations, such as the results of executing searching tasks. This bulletin board allows search tasks to be matched to the appropriate computer operating in parallel. Whenever one of the computers operating in parallel becomes idle, it will automatically check the bulletin board and process any appropriate searching tasks it finds there.

Sequence alignment is part of the process of comparing sequences for similarity, and may include introducing phase shifts or gaps into the query sequence or the sequences contained in the databases being searched in order to maximize the similarity between the sequences. Global alignment is the alignment of two sequences over their entire length, and local alignment is the alignment of a portion of two sequences.

The BLAST algorithm is a heuristic sequence similarity searching algorithm. For a given plurality of input query sequences and a given plurality of sequence databases, BLAST seeks to find one or more HSPs (high scoring pairs), each of which contains all or a portion of one sequence from the plurality of input sequences and all or a portion of one sequence from the plurality of sequence databases, such that the locally optimal ungapped alignment between the two members of said HSP achieves a score at least equal to a specified integer minimum score value or an e-score lower than a specified e-score threshold. Each such HSP will be reported by BLAST in a list ordered from best scoring HSP to worst scoring HSP, provided the total number of such HSPs does not exceed a specified cutoff value for the maximum number of descriptions and/or alignments to report. In the event that the total number of such HSPs does exceed said cutoff value, then BLAST truncates said list after reporting the maximum permitted number of HSPs.

For each input query sequence, BLAST operates by first finding one or more "words" (i.e., contiguous portions of a sequence in the plurality of databases) having length equal to a defined integer W (defaulted to W=3 in blastp), each of which has a local ungapped alignment with the input query sequence that achieves a score at least equal to a specified integer T when scored with a specified substitution matrix. Each such word is extended in both directions within the sequence that contains it in an attempt to find a locally optimal ungapped alignment between the input query sequence and said sequence having a score at least equal to the specified integer minimum score value or an e-score lower than the specified e-score threshold. When such a locally optimal ungapped alignment is found, BLAST forms an HSP whose members are the aligned portions of the input query sequence and said sequence from the plurality of databases.

Scoring of sequence comparison results is the process of quantitatively expressing the relatedness of one of the query sequences to one of the sequences contained in the databases being searched.

The raw score is the score of an alignment, or "S," calculated as the sum of substitution and gap scores.

The bit score, or S', is derived from the raw score, S, by taking into account the statistical properties of the scoring system used. As the bit scores have been normalized with respect to the scoring system, they can be used to compare alignment scores from different searches.

The e-score refers to the expectation value, which is the number of different alignments with scores equivalent or better than S that are expected to occur in a database search by chance. The lower the e-score, the more significant is the match.

The term sequence database or sequence databases means a collection or collections of known sequences against which the query sequence is compared. The database may be a private database or publicly available. For example, publicly available sequence databases are compiled and maintained by NCBI.

The term query sequence or query sequences means a sequence or sequences to be compared to the sequences contained in the databases being searched. A query sequence may be any biopolymer sequence of interest. For example, the sequence may be an amino acid sequence, a nucleic acid sequence, and the like.

A sequence in FASTA format begins with a single-line description, followed by lines of sequence data. The description line is distinguished from the sequence data by a greater-than (">") symbol in the first column. It is recommended by NCBI that all lines of text be shorter than 80 characters in length. Query sequences in the FASTA format are expected to be represented in the standard IUB/IUPAC amino acid and nucleic acid codes.

A gap is a space introduced into an alignment to compensate for insertions or deletions in one sequence relative to another. The insertion of gaps causes the deduction of a fixed amount, the gap score, from the alignment score, and extension of the gap to encompass additional monomers of the sequence is also penalized in the scoring of an alignment.

Substitution is the presence of a non-identical amino acid at a given position in an alignment. A conservative substitution is the substitution of an amino acid residue having similar physicochemical properties. Substitution in an alignment search affects the score through the use of a substitution matrix, which contains values proportional to the probability that a given amino acid will mutate into a second amino acid, for all pairs of amino acids.

II. Description of the Invention

The method and apparatus of the present invention allow for high-speed, high precision sequence comparison searching of one, two, three or more query sequences against one, two, three or more sequence databases. The method is implemented though the use of a group of computers operating in parallel, wherein the entire searching task to be performed is broken up into smaller searching tasks that are then processed by members of the group of computers operating in parallel, i.e., the worker computers. Each of the group of computers operating in parallel may be the same or different, and each of the group may have the same or different operating systems. In addition, if one of the computers operating in parallel should fail, the correctness and/or precision of the search results will not be affected. The method and apparatus of the present invention are independent of the searching program or algorithm used, and can be used with any publicly available or private database. Moreover, the search result generated, the unified search result, is identical to a search result that would have been generated if the searching task had not been partitioned into smaller searching tasks.

Each worker computer may assign to itself which searching tasks it will perform, and the partitioning of the query sequences and the partitioning of the sequence databases to create smaller searching tasks are done by each member of the group of computers operating in parallel. Such partitioning is based on, for example, the processing capability of each member of the group of computers operating in parallel, and may also be based on the total amount of processing capacity of the group of computers operating in parallel that can be used to perform the entire search task.

FIG. 1 is a flow chart providing an overview of an example of an implementation of the method of the present invention. Based on the teachings of the instant specification, other implementations would be apparent to the ordinary artisan. Initially, the entire job is a single large Task. Multiple smaller Tasks are created by splitting large Tasks. The new Tasks created by splitting a single Parent Task are called Buddy Tasks. The implementation depicted in FIG. 1 interleaves the processes of creating smaller searching tasks, executing those tasks, and merging the results of the smaller searching tasks to create the unified result of the entire searching task. A VSM bulletin board independent of the worker computers is used to store information about the ongoing searching process. For example, a list of searching tasks (the "Task List") and a list of results of executing the searching tasks (the "Result List") may be stored on the VSM bulletin board.

Initially, the list of searching tasks kept in the VSM bulletin board (i.e., the Task List) contains a single task representing the entire searching task. One or more worker computers may concurrently examine the searching tasks in the Task List. During the operation of the instant method, each worker computer of the computers operating in parallel may attempt to take (i.e., copy and remove, in an atomic operation) a task from the Task List. The VSM system, such as PARADIS-E.RTM. for the JAVA™ platform, ensures that each task may be taken by at most one of the worker computers that attempt to take a task. If there is an insufficient number of tasks on the Task List to permit each worker computer attempting to take a task to take at least one, then some of the worker computers attempting to take a task from the Task List may be forced to wait either until one or more additional tasks are added to the Task List, or until a signal to exit is received.

The execution of each searching task taken from the Task List creates a corresponding result that is stored in the list of search results kept in the VSM bulletin board (i.e., the Result List). The entire searching task is complete when the Result List contains exactly one result that is the result for the entire searching task.

The execution of each searching task makes use of a number of parameters, such as cut-off values, that control the operation of the searching method (e.g., BLAST) and may affect the results that are computed. For each searching task taken from the task list, the instant method makes use of exactly the same set of parameters as would have been used for the entire searching task not using the apparatus and method of the instant invention. As described below, this enables the method to report a unified result for the entire searching task that is identical to the result that would be obtained if the apparatus and method of the instant invention were not used. As also described below, the method and apparatus of the instant invention, however, allow for super-linear speedup in generating the sequence comparison result.

One or more worker computers may concurrently examine the results in the Result List. During the operation of the instant method, one or more of the worker computers operating in parallel may attempt to take (i.e., copy and remove, in an atomic operation) a result from the Result List. The VSM system ensures that each result may be taken by at most one of the worker computers that attempt to take a result. If there is an insufficient number of results on the Result List to permit each worker computer attempting to take a result to take at least one, then some of the worker computers attempting to take a result from the Result List may be forced to wait either until one or more additional results are added to the Result List, or until a signal to exit is received.

Execution of a searching task requires some quantity of computational resources (e.g., memory, disk, CPU time, etc.), and upon taking a task, a worker computer estimates the quantity of computational resources required to execute the task. This estimate is termed "RES(Task)." RES(task) is too large if it exceeds the resources available on the computer. If RES(Task) is too large for that particular worker computer, the worker computer will divide the searching task into two smaller searching tasks and add one of them to the Task List kept in the VSM bulletin board. RES(Task) will then be recalculated for the one of the two smaller searching tasks retained by the worker computer. The two smaller searching tasks that are the parts of the now-divided searching task are termed "Buddies.". Each new smaller searching task is marked as the other one's Buddy, and the original undivided task is marked as the "Parent" of each of the two new smaller searching tasks.

Once a worker computer obtains a task for which RES (Task) is not too large, it then estimates the fraction of the remaining computational effort represented by the task, termed GRAN(Task), and determines if it is too large. GRAN (Task) is too large if it exceeds a defined constant parameter times the ratio of the estimated computational power of the worker computer in question to the estimated total computational power of the aggregate of computers that the worker computer in question believes to be operating in parallel at the current time. If GRAN(Task) is too large, the worker computer goes through a similar process of dividing the searching task into two smaller searching tasks and retaining one of them as is performed when RES(Task) is too large.

Once the worker computer has a searching task for which neither RES(Task) or GRAN(Task) is too large, it executes the searching task and computes the result for that searching task. The searching task may be executed using any desired algorithm, such as the BLAST algorithm. The searching task is termed the worker computer's "Present Task," and the computed result is termed the worker computer's "Present Result." Executing Task creates the corresponding Present Result.

The worker computer then performs an examination of its Present Task and Present Result to decide what to do next. First, the worker computer determines whether its Present Task is the entire searching task. To do this, the worker computer looks at the VSM bulletin board to determine whether its Present Task has a Buddy Task. If its Present Task has no Buddy Task, then its Present Task is the entire searching task, and its Present Result is the final result for the entire searching task. In such a case, the worker computer adds its Present Result to the Result List kept in the VSM bulletin board, which will then contain exactly one result (i.e., the result for the entire searching task). At that point, the entire searching task is complete, and the worker computer then signals any waiting worker computers to exit.

If the worker computer's Present Task does have a Buddy Task, then the worker computer attempts to create a unified result for the Parent Task of its Present Task. The worker computer first looks at the VSM bulletin board to determine if the Buddy Task's result is READY, for example by searching for that result on the Result List kept in the VSM bulletin board. If it is not READY, the worker marks its Present Result as READY and adds it to the Result List kept in the VSM bulletin board. The worker computer then selects and executes another searching task if one is available on the Task List kept in the VSM bulletin board. If none is available, it waits either for a searching task to be added to the Task List, or for the signal to exit. Thus each of the group of computers operating in parallel may perform one, two, or more searching tasks during the operation of the instant method.

If the Buddy Task's result is READY, then it will be on the Result List kept in the VSM bulletin board. The worker computer then takes the Buddy Task's result from the Result List and merges its Present Result with the Buddy Task's result to produce a unified result for the Parent Task of its Present Task (which is also the Parent Task of the Buddy Task). The worker computer then discards information about its Present Task, the Buddy Task, its Present Result, and the Buddy Task's result. The worker computer then designates the Parent Task as its Present Task, and the Parent Task's unified result as its Present Result.

The worker computer then goes through similar examination and subsequent processing for its new Present Task and Present Result (which were previously known as the Parent Task and the Parent Task's unified result) as it did for its previous Present Task and previous Present Result. This examination and merging process is reiterated until either the worker computer determines that it has formed, as its then Present Result, the final result for the entire searching task, or the worker computer finds that the result of the Buddy Task of its then Present Task is not yet READY.

In the former case, the worker computer places its Present Result on the Result List kept in the VSM bulletin board, which will then contain exactly one result (i.e., the final result for the entire searching task). At that point, the entire searching task is complete, and the worker computer then signals any waiting worker computers to exit.

In the latter case, the worker computer marks its then Present Result as READY and adds it to the Result List kept in the VSM bulletin board. It then selects and executes another searching task if one is available on the Task List kept in the VSM bulletin board. If none is available, it waits either for a searching task to be added to the Task List, or for a signal to exit.

Eventually, the reiteration of the task selection/execution and result merging processing will cause all of the searching tasks to be selected and executed, and all of the computed task results to be merged together to form a single, unified result for the entire searching task. Thus, the method will produce the correct result for the entire searching task.

FIGS. 2A, 2B, 3A through 3Q, 4, and 5 demonstrate in more detail how the entire searching task is divided up into smaller searching tasks to be performed by each of the computers operating in parallel. FIG. 6 contains several charts that illustrate the performance of the method of the present invention in comparison with a standard execution of NCBI BLAST on a single computer of the same speed as the worker computers used for the method. As is evident from the charts, a substantial, superlinear speedup may be achieved using the method.

Figure 2B:
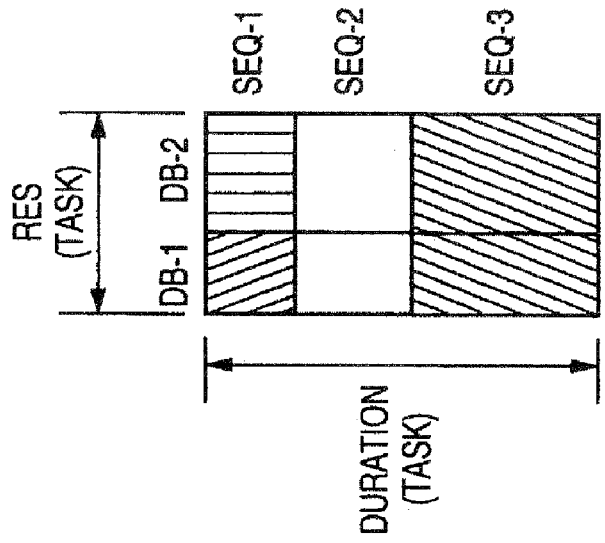
FIGS. 2A and 2B illustrate a rectangular graphical representation of searching tasks that is used to describe the method of the invention.
Figure 2A:
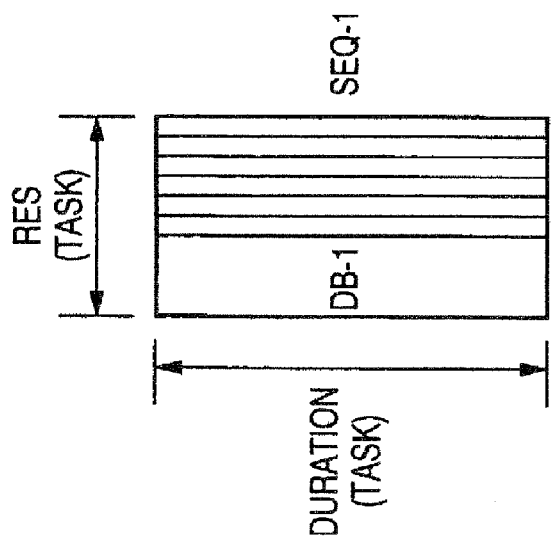

As illustrated in FIGS. 2A and 2B, the entire searching task to be performed may be represented by a rectangle, with the horizontal representing the one or more databases against which the query sequences are to be compared, and the vertical representing the query sequences themselves. Any sequence database may be used, such as the sequence databases derived from the databases maintained by the National Center for Biotechnology Information (NCBI). FIG. 2A illustrates a representation of one Task searching a single sequence against 2 databases. FIG. 2B illustrates a representation of one Task searching 3 sequences against 2 databases.

The length of the rectangle's horizontal can be correlated to RES(Task), or the estimated quantity of computational resources required to execute the task. For efficient operation, it is only necessary for RES(Task) to estimate the quantity of the most important computational resources required to execute the task. For BLAST, RES(Task) should estimate the amount of memory required to execute the task, since the memory is the most critical computational resource for BLAST. The memory requirement for BLAST is largely dependent on the size of the sequence database or portion thereof that is to be searched. Thus, one possible estimate for RES(Task) is equal to the sum of the length of the largest query sequence or portion thereof in the task plus the total length of the sequences in the database or portion thereof, all in FASTA format, times 1.2.

If RES(Task) is too large, a vertical boundary is defined between individual databases or within a database, such as a boundary that most evenly divides the large rectangle representing the undivided searching task into two smaller rectangles. This introduction of a new vertical boundary is illustrated, for example, in FIG. 3B, where the boundary is introduced between two databases. This process may allow for rearrangement of databases along the horizontal in order to create a more even division without defining a boundary within a database, or in order to enable a worker computer to create searching tasks that use databases already stored in the memory of the worker computer in question.

Figure 3A:
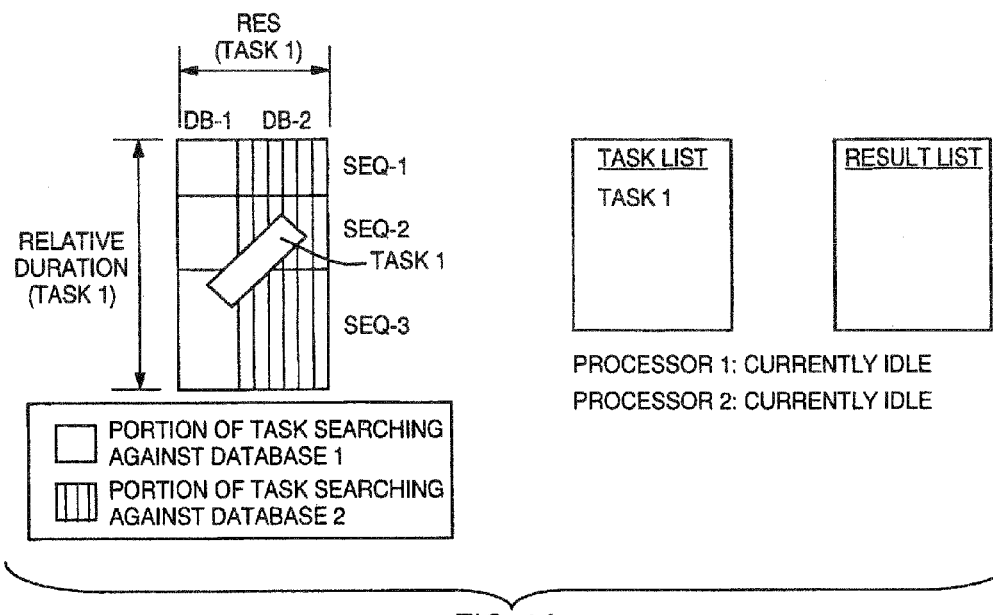
FIGS. 3A through 3Q are multipart figures that provide a detailed example of the application of the method described in FIG. 1.

The method also allows for the individual databases themselves to be split up to permit creation of searching tasks for which RES(Task) is not too large for a given worker computer. This is illustrated in FIG. 3D. Preferably, the databases are split at defined positions, such as in half, in quarters, etc., so that the results computed for each individual searching task may be more easily merged to provide the unified result. This is not, however, a requirement of the method.

The vertical of the rectangle in FIGS. 2A and 2B can be correlated to the relative duration of the task in question, where the duration of any searching task may be measured, for example, by the time in seconds required to execute the searching task with the particular query sequences and the database or portion thereof. The relative duration of the task in question is then equal to the fraction of the duration of the undivided entire searching task represented by the duration of the task in question.

The first division of the searching task using the estimate of RES(Task), i.e., along the horizontal, splitting up the databases, is related to the quantity of computational resources, such as memory, available on the worker computer. The second division of the searching task, i.e., along the vertical, by splitting up the query sequences, as illustrated in FIG. 3C, is related to the estimated relative duration of the searching task. In order to obtain the largest possible speedup, the method tries to ensure (1) that executed searching tasks are small enough, i.e., of sufficiently short relative duration, so that there will be enough tasks to fully occupy all of the worker computers available for the entire searching task, and (2) that executed searching tasks are large enough, i.e., of sufficiently long duration, that the amount of overhead related to the use of parallelism (i.e., the costs related to communication, access to the VSM, and task startup or shutdown on the individual worker computers) are small enough that the overall method is efficient. By ensuring these two properties, the method is able to achieve linear speedup attributable to the full and efficient use of all of the worker computers available to perform the entire searching task. In practice, however, the method often achieves superlinear speedup because the divisions based on RES(Task) reduce the amount of I/O overhead, which leads to additional speedup beyond the linear speedup that would be expected normally.

In order to perform the second type of division, i.e., along the vertical, by splitting up the query sequences, the method makes use of an estimate of the granularity of the task. The granularity of a task relates (1) the fraction of the duration of the undivided entire searching task represented by the task at hand, to (2) the fraction of the total available computational processing capacity represented by the worker computer in question. The computational processing capacities of the computers may be estimated in various ways, for example, by estimating their speeds (measured, for example, in residues or bases searched per second). The method does not require that any specific estimation technique be used.

The fraction of the duration of the undivided entire searching task represented by the task at hand can be estimated by: t/T where:

t is the estimated duration of the particular searching task at hand when executed on the worker computer, ignoring any effects due to limited amounts of memory; and T is the estimated duration of the undivided entire searching task when executed on the worker computer, ignoring any effects due to limited amounts of memory. Since the computed quantity is a ratio of durations, it does not matter what computer is used as a reference for estimating the durations, since properties of the reference computer, such as its speed, will not affect the ratio.

The fraction of the total computational processing capacity represented by the worker computer in question can be estimated by: p/P where:

p is the estimated processing capacity of the worker computer in question; and

P is the estimated aggregate processing capacity of all of the worker computers believed by the worker computer in question to be available to perform the remaining incomplete searching tasks.

The granularity of the task can then be estimated by:

$$GRAN(\text{Task}) = \frac{t}{T} / \frac{p}{P}$$

In order to obtain the largest possible speedup, the method tries to ensure that GRAN(Task) satisfies:

$c_1 > GRAN(\text{Task}) > c_2$ where:

$c_1$ and $c_2$ are user defined tuning constants. For example, $c_1$ and $c_2$ may be defined as 0.5 and 0.25, respectively.

If GRAN(Task) is too large, the query sequences are divided into two parts so that the corresponding searching tasks that result have nearly equal values of GRAN(Task). If required, each individual query sequence may be divided into smaller query subsequences.

The method allows that if GRAN(Task) is too small, the task at hand may be increased in size. This may be done, for example, by combining the task at hand with another task on the Task List.

For each sequence database or portion thereof created by the task division process just described, a counter is kept in the VSM bulletin board of the number of remaining incomplete searching tasks that reference that sequence database or portion thereof. Whenever a worker computer has an opportunity to select a new searching task, it will, if possible, "fixate" by selecting a task that searches the same database or portion thereof as its just-completed task, because that database or portion thereof is already loaded into the worker computer's memory. This reduces I/O overhead and improves performance greatly. Initially, each worker computer chooses a database or portion thereof on which to fixate using a weighted random variable so that the chance of choosing a particular database or portion thereof depends on the frequency of that database's representation in all remaining incomplete searching tasks. Once a worker has chosen a database or portion thereof, it will only take tasks that reference that database or portion thereof, subject to the following two limitations:

(1) If there is no task on the Task List that references that database or portion thereof, the worker will wait idle for a short time ("$t_{idle}$"), and then, if there is still no such task on the Task List, the worker will repeat the database selection process, undoubtedly deciding to fixate on a new database or portion thereof; and (2) After remaining fixated for a certain time span (the "quantum") the worker will repeat the database selection process, most likely deciding to fixate on a different database or portion thereof.

The user of the method can specify the values of both $t_{idle}$ and the quantum. An example of appropriate settings would be 10 seconds for $t_{idle}$ and 30 minutes for the quantum.

Limitation (1) is designed to ensure that no worker computer remains idle for a long time waiting for tasks referencing a particular database or portion thereof; this could happen without the limitation if all such tasks had been executed. Limitation (2) is designed to ensure that the worker computers in aggregate are spread reasonably uniformly across all incomplete searching tasks.

The final result of the method is a unified search result for the entire searching task. As when using any sequence alignment algorithm, such as BLAST, the result is a list of the zero, one, two or more sequences (termed "hits") from the database or databases that have the greatest similarity to the query sequence or query sequences. Typically, each hit in the list is reported along with a numerical score that corresponds to the degree of similarity between the hit and one or more of the query sequences. In that case, the list of hits may be ordered by either decreasing value of the raw score of each hit or increasing value of the normalized e-score of each hit.

The user may define "cut-offs" to limit the number of hits included in the output for the entire searching task. For example, the user can limit the absolute number of hits or can specify threshold values on the size of the raw score or the e-score for each reported hit.

The method allows for various ways of computing the unified result for the entire searching task from the results for each of the smaller searching tasks created using the division processes described above. For example, all of the results for the smaller searching tasks could be collected by one of the worker computers operating in parallel, and one of the results could be designated as that worker computer's Present Result. The worker computer in question could then build the unified result for the entire searching task by reiterating a process of pairwise merging in which one of the results for the smaller searching tasks is merged with the worker computer's Present Result. When all of the results for the smaller searching tasks have been merged with the worker computer's Present Result, that Present Result will be the unified result for the entire searching task.

As noted above, FIG. 1 is a flowchart depicting an example of implementing the instant method, which interleaves the processes of task division, task execution, and creation of the unified result for the entire searching task. This implementation of the creation of the unified result for the entire searching task may be more efficient than the simple implementation just described because it involves less overhead related to the use of the VSM bulletin board. The detailed examples of FIG. 3A through 3Q illustrate the sequence of task divisions and result mergings that might be achieved by the method using the implementation of FIG. 1.

Whichever of the implementations is used to create the unified result for the entire searching task from the results of the smaller searching tasks, the computation is performed as a sequence of pairwise result merges. In each one, a new result is created by merging two existing results using the following process:

(1) First, the sequence hits in the old results are interleaved in order of decreasing raw score;

(2) Next, the e-score for each of the sequence hits is adjusted as described below; and (3) Last, any cut-offs used to limit the number of sequence hits reported for each searching task are applied to limit the number of sequence hits reported in the new result.

In (2) of this process, it may be necessary to recalculate the e-scores to take into account the partitioning of the sequence database or databases, so that the results that are reported are the same as if the entire searching task had never been broken up into smaller searching tasks. If each of the existing results corresponds to searching tasks referencing the same databases or portions thereof, then no recalculation is required, and the e-score reported for each sequence hit in the new result will be the same as the one reported in one or both of the existing results for the same sequence hit. If, however, the existing results correspond to searching tasks referencing different databases or portions thereof, the e-scores must be recalculated. If the letters B and C represent two different databases, the number of letters in database B can be represented by B', and the number of letters in database C can be represented by C'. Then the e-score for each sequence hit in database B is recomputed using the following formula:

$$escore_{new} = escore_{orig} \cdot \left[ \frac{B' + C'}{B'} \right]$$

Similarly, the e-score for each sequence hit in database C is recomputed using the following formula:

$$escore_{new} = escore_{orig} \cdot \left[ \frac{B' + C'}{C'} \right]$$

As noted earlier, users often make use of cut-offs to limit the number of sequence hits reported by search methods such as BLAST. The instant method intends to produce essentially the same result (i.e., exactly the same result, up to minor reorderings or variations due to limitations of computer floating-point arithmetic) for the entire searching task as would have been reported without division into smaller searching tasks. To do this, the method must properly apply the same user-specified cut-offs.

Executing a searching task has the effect of implicitly creating an internal list of sequence hits ordered by decreasing raw score. Cut-offs limit the number of sequence hits included in the result for the searching task by discarding all but the best sequence hits from the internal list. For example, a cut-off might limit the number of hits to an absolute number of the best ones, or it might limit the hits to those with raw score exceeding some threshold or those with e-score below some threshold. In all cases, the particular set of sequence hits that survive the cut-off may depend on the relative ordering of the sequence hits in the internal list. Note that except for random reorderings or minor variations due to the limited accuracy of computer floating-point arithmetic, the internal list would be unchanged if it were ordered by increasing e-score instead of decreasing raw score.

Now consider any sequence hit that survives the application of cut-offs for the undivided entire searching task, i.e., the entire searching task as executed by the original BLAST method without division into smaller searching tasks. That hit is in one of the databases referenced by the entire searching task, and it must have survived the cut-offs because its achieved raw score, when compared to some one of the query sequences in the entire searching task (termed the "matching query sequence"), was sufficiently high relative to the raw scores of other hits.

The division process described above guarantees that at least one of the smaller searching tasks generated by the instant method must:

(1) reference a subdatabase of the databases referenced in the entire searching task that contains the sequence hit in question; and (2) include the matching query sequence among its query sequences.

Certainly, the matching query sequence will be compared to the sequence hit in question during the execution of this particular smaller searching task. Since raw scores depend only on the particular pair of sequences compared, it is clear that the sequence hit in question will achieve a raw score for the smaller searching task that is equal to the raw score reported for the undivided entire searching task. Moreover, since the one or more subdatabases referenced by the smaller searching task in question form, in aggregate, a subset of the databases referenced by the undivided entire searching task, the subdatabases will contain no more high quality sequence hits than the aggregation of databases referenced by the undivided entire searching task. Hence, the sequence hit in question will be no further from the beginning of the internal ordered list for the smaller searching task in question than it is in the internal ordered list for the undivided entire searching task. Therefore, since the sequence hit in question survives the cut-offs in the undivided entire searching task, it must also survive the same cut-offs in the smaller searching task.

This argument demonstrates that each sequence that survives the cut-offs for the undivided entire searching task also survives the cut-offs for at least one of the smaller searching tasks created by the instant method provided that the same cut-offs are applied to those tasks. In order to demonstrate that such a sequence also appears in the final result computed by the instant method, it is necessary to verify that (3) in the above process for result merging never eliminates the sequence.

Suppose that the two old results being merged contain all of the sequences meeting the cut-offs for the corresponding smaller searching tasks. By the fact that it interleaves based on raw score, it is clear that the interleaving performed in (1) produces a list of sequence hits in which, except for some potential random reordering of hits with equal scores, the sequence hits are in the same relative ordering (by decreasing raw score) as they are in the internal list for the undivided entire searching task. The effect of applying a cut-off to the interleaved list then depends on the type of cut-off. If the cut-off limits the number of sequence hits to some absolute maximum number, then taking that absolute maximum number of sequences from the beginning of the interleaved list is guaranteed to be sufficient to permit eventual creation of the proper result for the entire searching task. At worst, later merging will discard some of the included sequences in favor of others with higher scores.

If the cut-off limits the sequence hits based on a raw score threshold, then it is sufficient to include any sequence hit from the interleaved list that has a raw score equaling or exceeding the threshold raw score. Since each of the two old results now being merged already contains all of the sequence hits from the corresponding smaller searching task that meet the raw score threshold criterion, it is clear that the new merged result will do so as well, and that further merges used to create the unified result for the entire searching task will pass these sequence hits on to the unified result.

If, instead, the cut-off limits the sequence hits based on an e-score threshold, then it is sufficient to include any sequence hit from the interleaved list that has an e-score no greater than the threshold raw score. According to the formulae used to adjust the e-scores in (2), merging may increase, but will never reduce, the e-score for any particular sequence hit. Therefore, no sequence hit in the interleaved list that is excluded by the cut-off (because its e-score is too large) will ever achieve an e-score that is small enough to pass the cut-off test. Similarly, none of the sequence hits eliminated by the cut-off in an earlier merging could possibly meet the cut-off test at this stage of merging.

As a result of the above analysis, it appears that the instant method does, in fact, produce essentially the same result (i.e., exactly the same result, up to minor reorderings or variations due to limitations of computer floating-point arithmetic) for the entire searching task as would have been reported by ordinary BLAST without division into smaller searching tasks.

III. EXAMPLES

A. Example 1

FIG. 3A through 3Q provide a detailed example of the application of the method of the instant invention using the implementation of FIG. 1. Each of FIGS. 3A through 3Q shows the representation of the entire searching task at a particular time point during a sample operation of the method of the invention when run on two processors. In addition to the representation of the tasks, FIGS. 3A through 3Q also show the contents of 2 important lists on the bulletin board (i.e., the Task List and the Result List) and indicates the current activities for each of the two participating processors at the corresponding instant of time. The Entire Task is "Task 1". Tasks created by splitting larger divisions are denoted by names using dotted notation in which either the Parent Task's name is extended with a period (".") followed either by a capital letter or an Arabic numeral. Capital letters are used when vertical splitting is performed based on RES(Task), as when Task 1.A and Task 1.B denote the two tasks created by subdividing Task 1. Arabic numerals are used when horizontal splitting is performed based on GRAN(Task), as when Task 1.A.1 and Task 1.A.2 denote the two tasks created by subdividing Task 1.A. The computation in question entails the searching of a group of query sequences against two databases using two processors (i.e., worker computers). Each of FIG. 3A through FIG. 3Q is a representation of the state of the computation at a particular instant in time. (FIG. 4 contains timelines showing the activities of the processors between the time points that correspond to the subfigures. FIG. 4 also contains lettered markings that correlate to FIGS. 3A through 3Q to their specific points in time during the computation.) the processor activities are correlated with FIG. 4, which illustrates the details of the processor activity and includes a time line that is correlated to FIG. 3A through 3Q.

Each of FIGS. 3A through 3Q contains four sections reflective of the states of the searching task, the processors and the VSM bulletin board at the time point in question:

(1) A rectangular representation similar to those of FIGS. 2A and 2B that represents the entire searching task as subdivided into smaller searching tasks at the time point in question;

(2) An illustration of the Task List and the Result List stored in the VSM bulletin board at the time point in question;

(3) A textual description of the present activities of the worker computers at the time point in question; and (4) A caption describing the current state of the searching task(s) and the change(s) from the previous subfigure.

The Legend included in FIGS. 3A through 3Q illustrate describes the graphical markings and the Task naming conventions used in the example. Similar markings are used in FIGS. 4 and 5, as well.

Figure 3B:
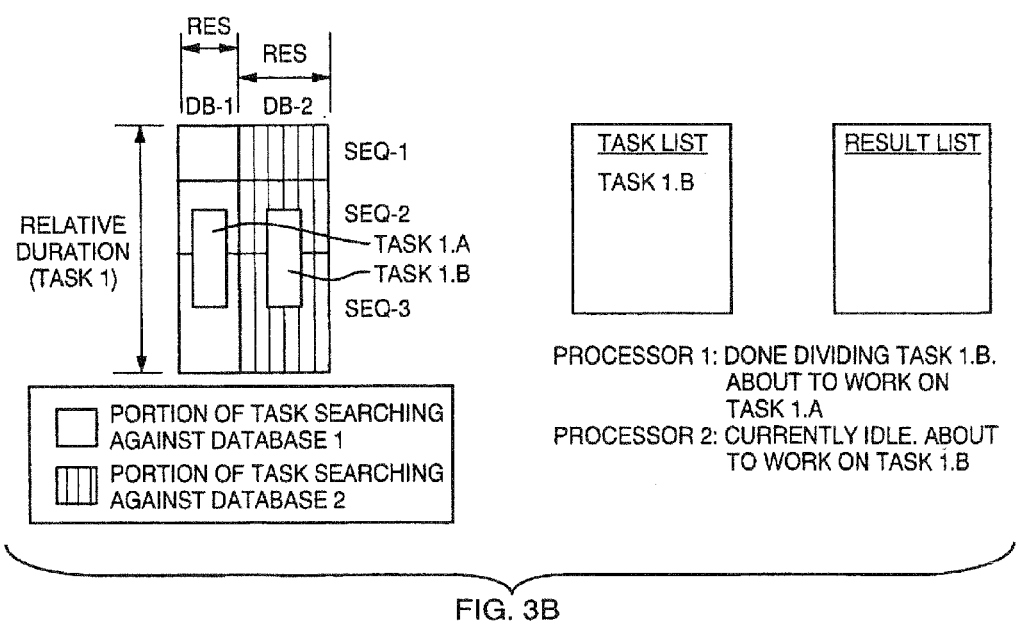
FIG. 3B illustrates a graphical representation of Processor 1 dividing Task 1 vertically (Flowchart Box B); keeps Task 1.A.
Figure 3C:
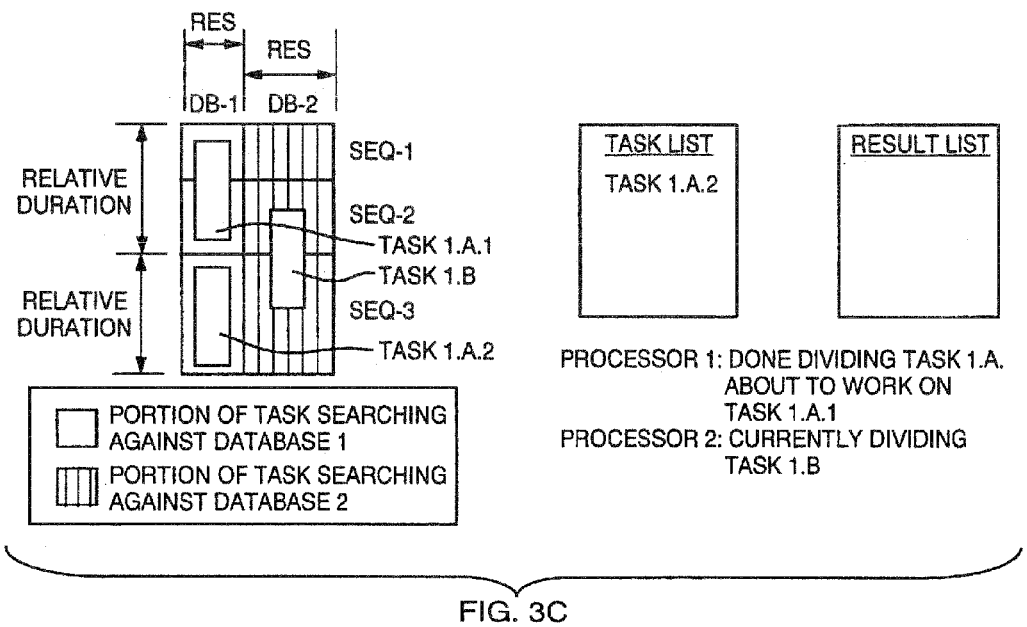
FIG. 3C illustrates a graphical representation of Processor 1 dividing Task 1.A horizontally (Box C); keeps band begins executing Task 1.A.1.
Figure 3D:
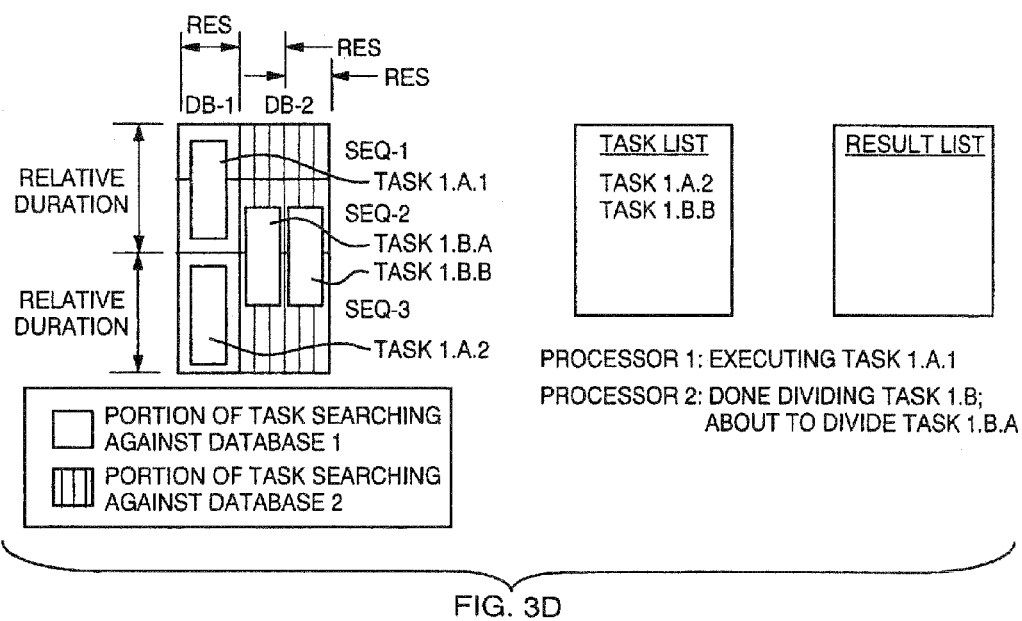
FIG. 3D illustrates a graphical representation of Processor 2 dividing Task 1.B vertically (Box B); keeps Task 1.B.A.

FIGS. 3A through 3Q illustrate the most important operations in the method using the implementation of FIG. 1:

(1) FIGS. 3B and 3D illustrate the division of tasks by dividing and/or rearranging one or more databases (i.e., represented as the introduction of a new vertical boundary).

Figure 3E:
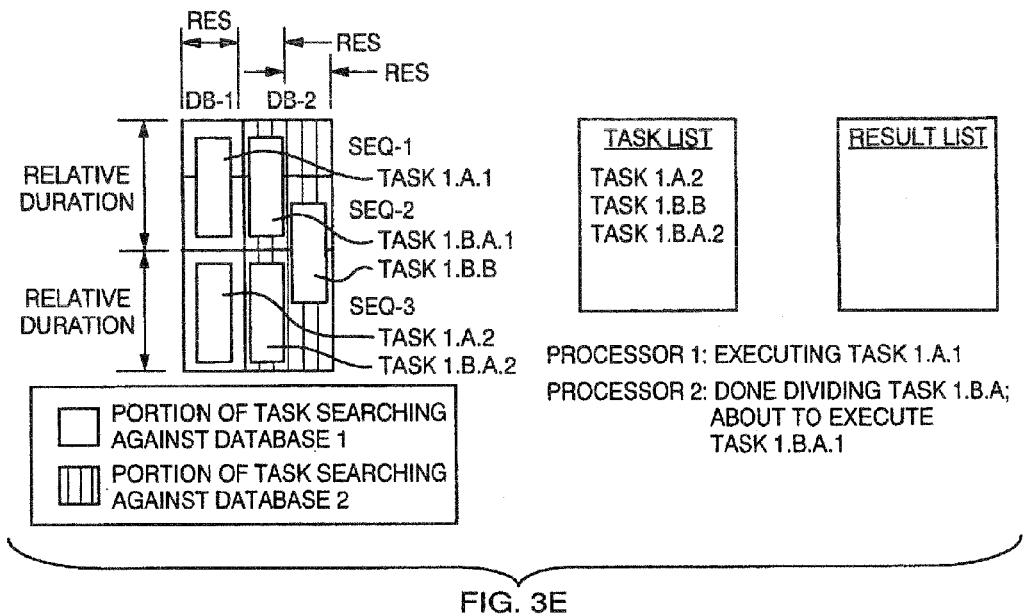
FIG. 3E illustrates a graphical representation of Processor 2 dividing Task 1.B.A horizontally (Box C); keeps and begins executing Task 1.B.A.1.
Figure 3F:
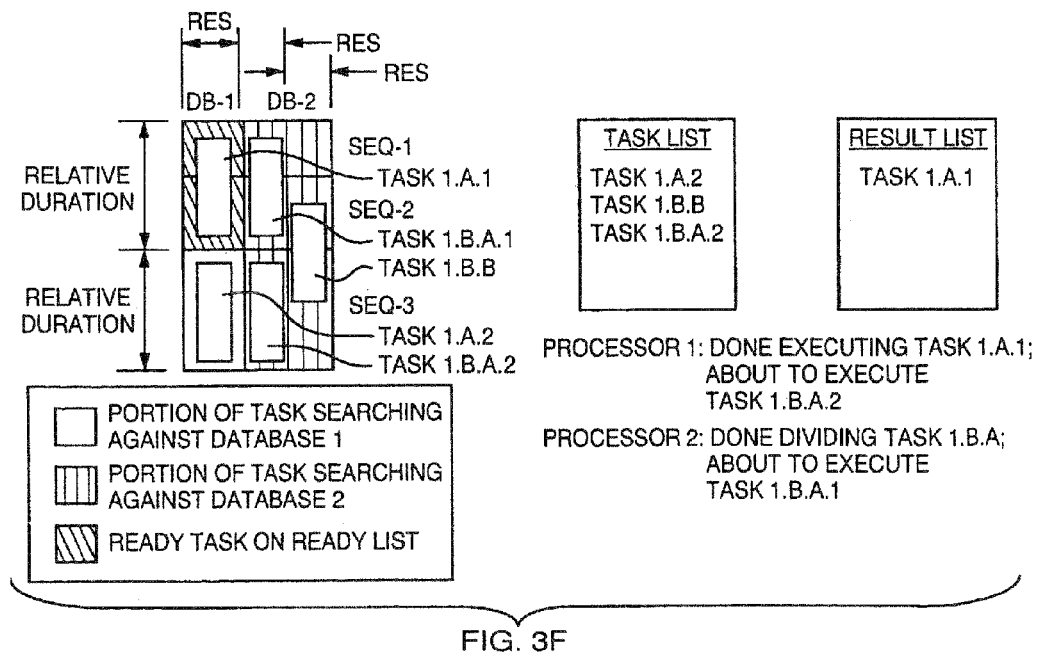
FIG. 3F illustrates a graphical representation of Processor 1 completing Task 1.A.1 (Box D); marks it READY (Box A).
Figure 3G:
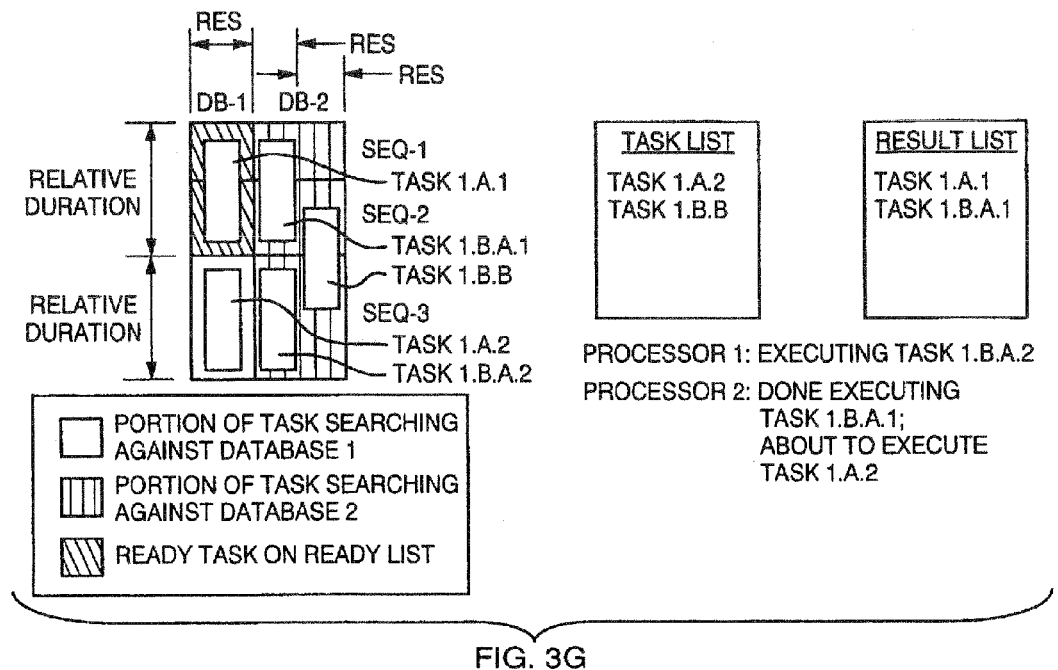
FIG. 3G illustrates a graphical representation of Processor 2 completing Task 1.B.A.1 (Box D); marks it READY (Box A).
Figure 3H:
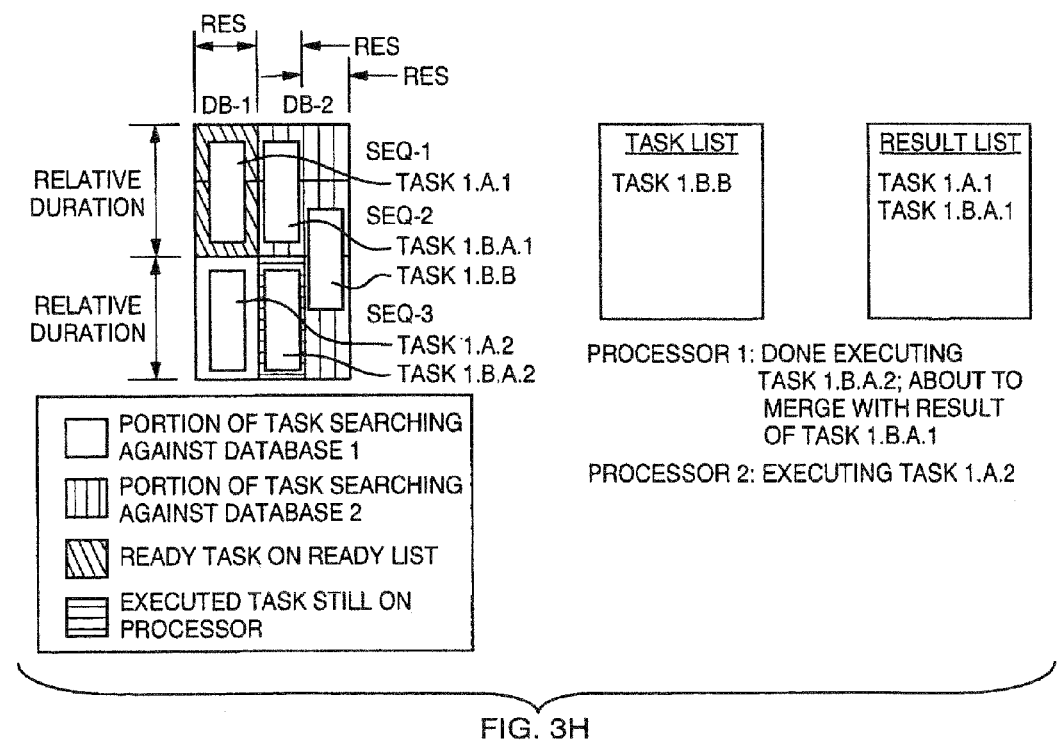
FIG. 3H illustrates a graphical representation of Processor 1 completing Task 1.B.A.2 (Box D).
Figure 3I:
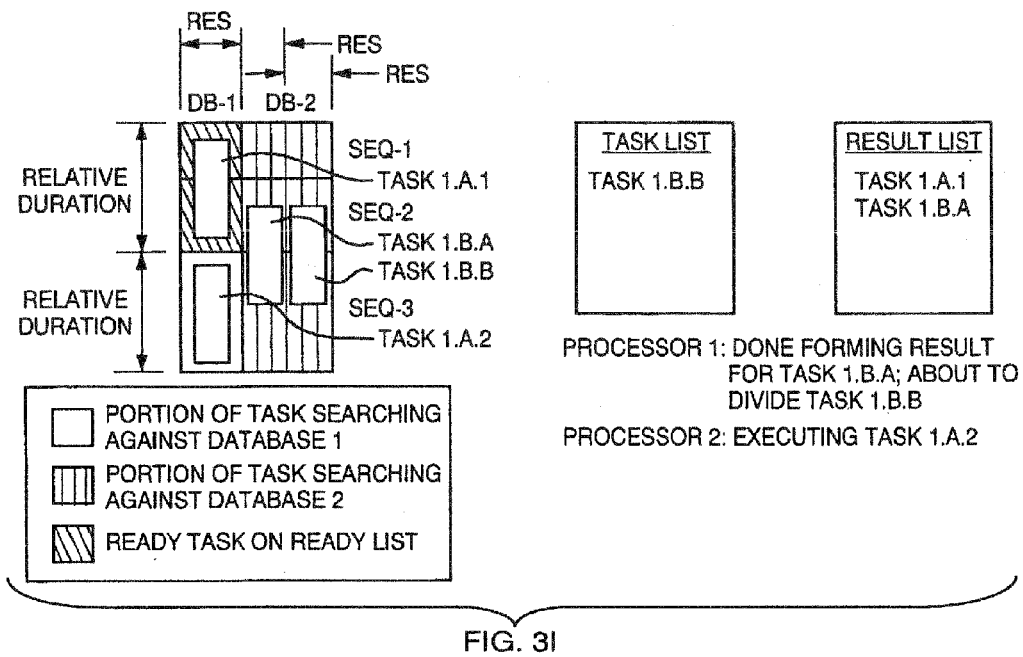
FIG. 3I illustrates a graphical representation of Processor 1 merging result for Task 1.B.A.2 with result for Buddy Task 1.B.A.1, thereby computing result for Parent Task 1.B.A. (Box E); marks Task 1.B.A. READY since Buddy Task 1.B.B. is not READY.
Figure 3J:
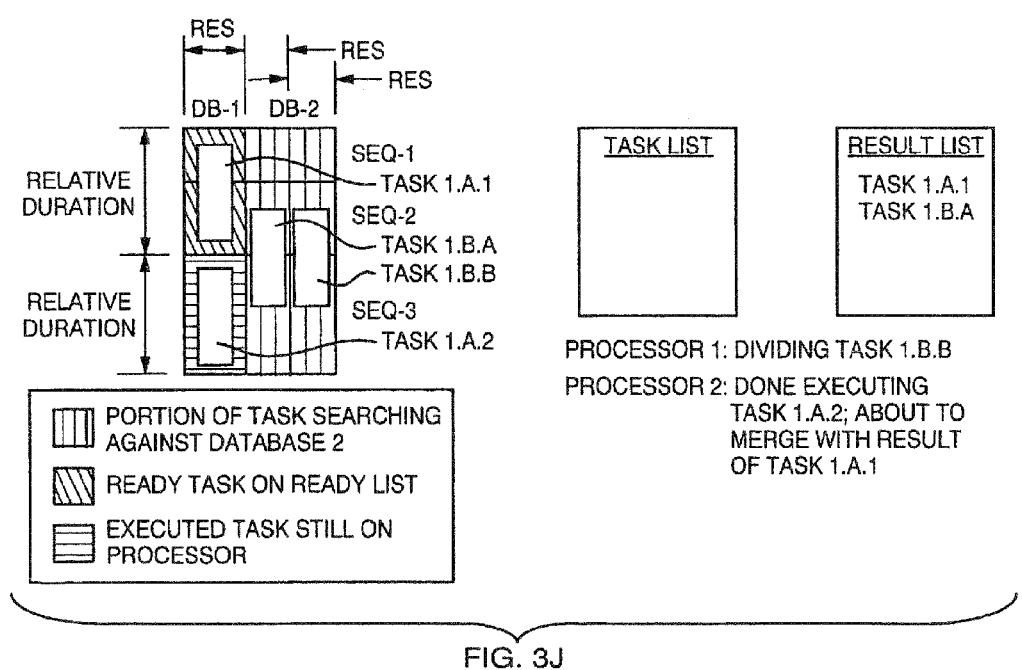
FIG. 3J illustrates a graphical representation of Processor 2 completing Task 1.A.2 (Box D).
Figure 3K:
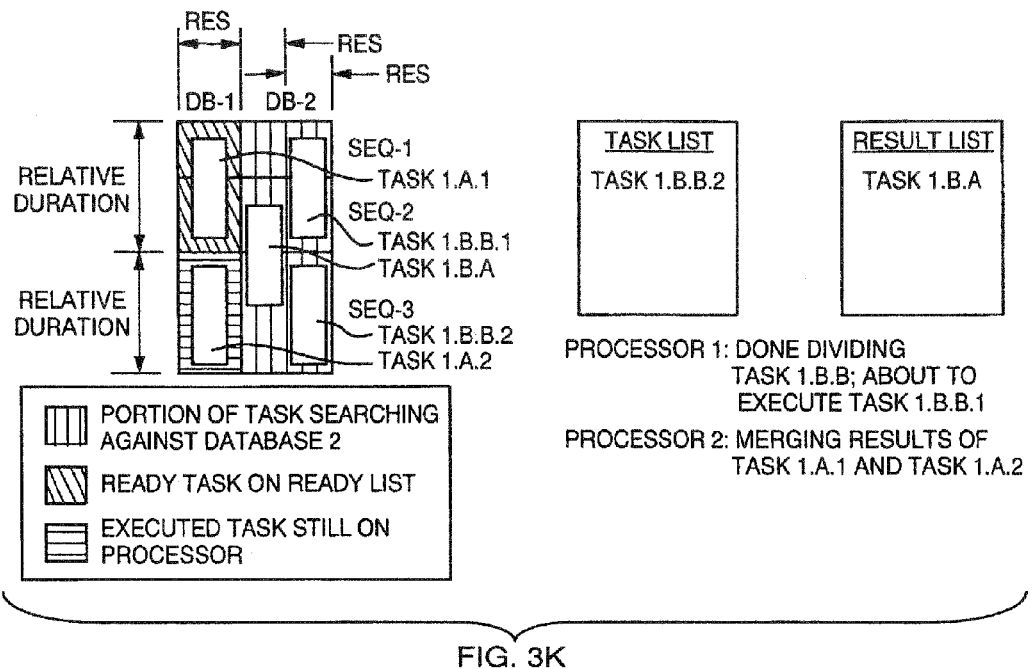
FIG. 3K illustrates a graphical representation of Processor 2 dividing Task 1.B.B. horizontally (Box C); keeps Task 1.B.B.1.
Figure 3L:
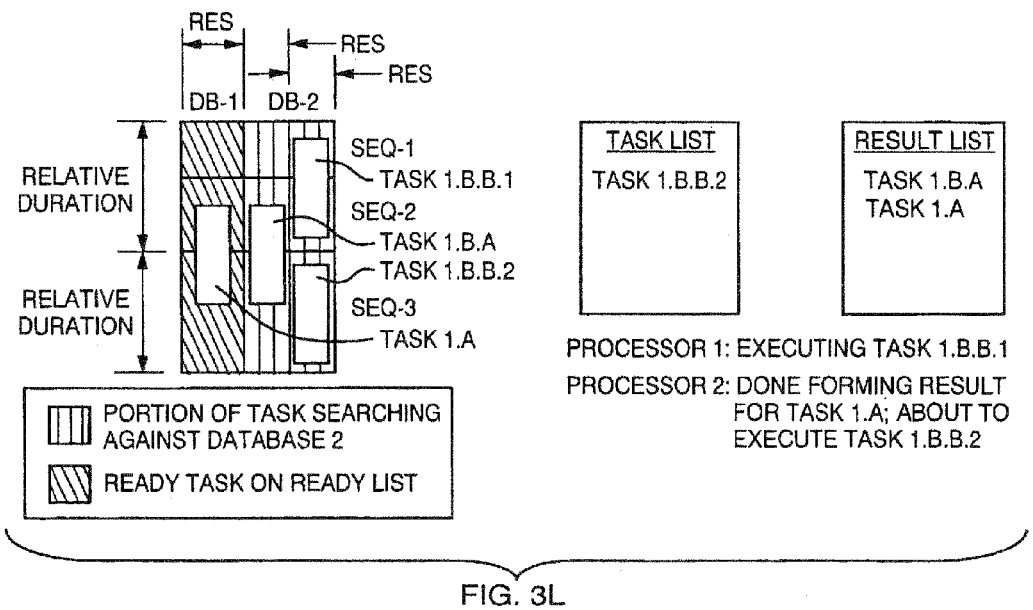
FIG. 3L illustrates a graphical representation of Processor 2 merging result for Task 1.A.2 with result for Buddy Task 1.A.1, thereby computing result for Parent Task 1.A. (Box E); marking Task 1.A. READY, since its Buddy Task 1.B is not ready.

(2) FIGS. 3C, 3E and 3K illustrate the division of tasks by dividing the query sequences (i.e., represented as the introduction of a new horizontal boundary).

Figure 3M:
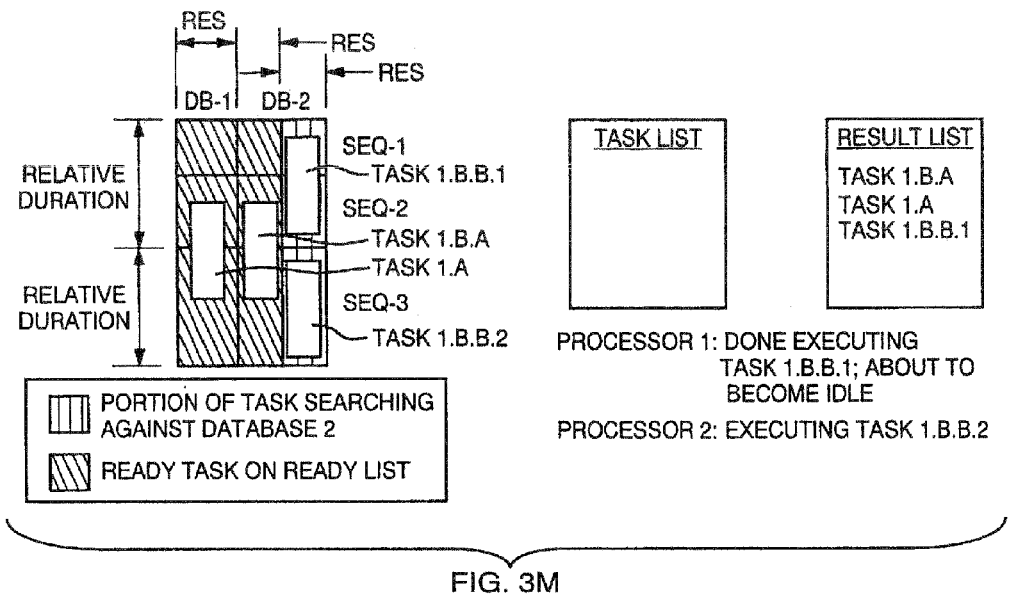
FIG. 3M illustrates a graphical representation of Processor 1 completing Task 1.B.B.1 (Box D) marking it READY (Box A) since Task 1.B.B.2 is not READY.
Figure 3N:
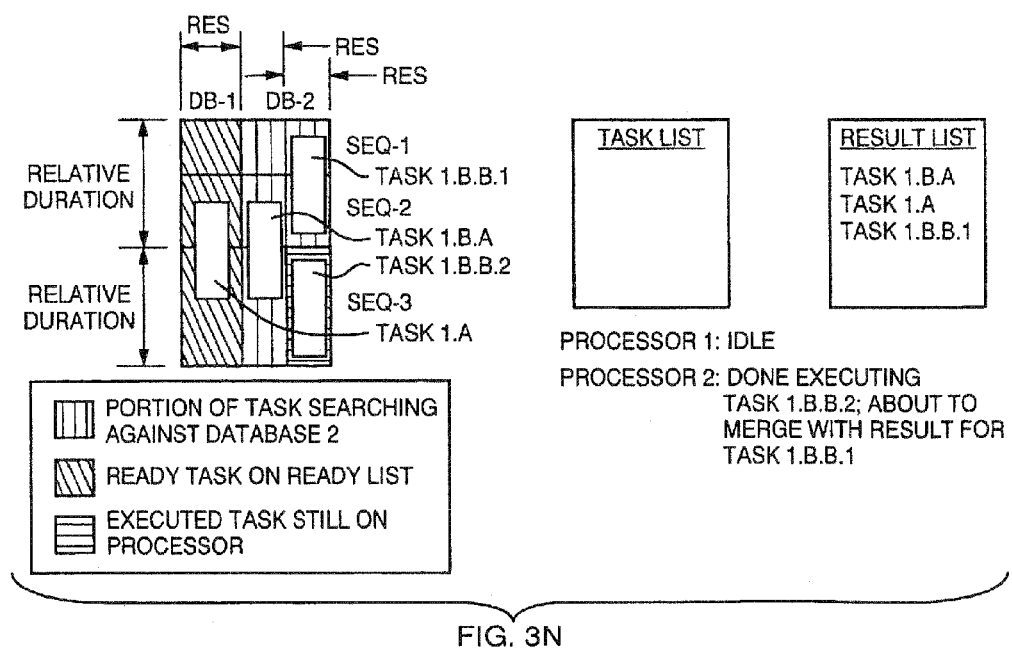
FIG. 3N illustrates a graphical representation of Processor 2 completing Task 1.B.B.2 (Box D).

(3) FIGS. 3F, 3G and 3M illustrate the result of executing a task which has a Buddy Task that is not READY.

(4) FIGS. 3I and 3L illustrate the case of performing a single merging that leads to a unified task for which no further unification is possible until other tasks have been completed. (Such tasks are marked as READY and placed on the Result List in the VSM bulletin board.)

Figure 3O:
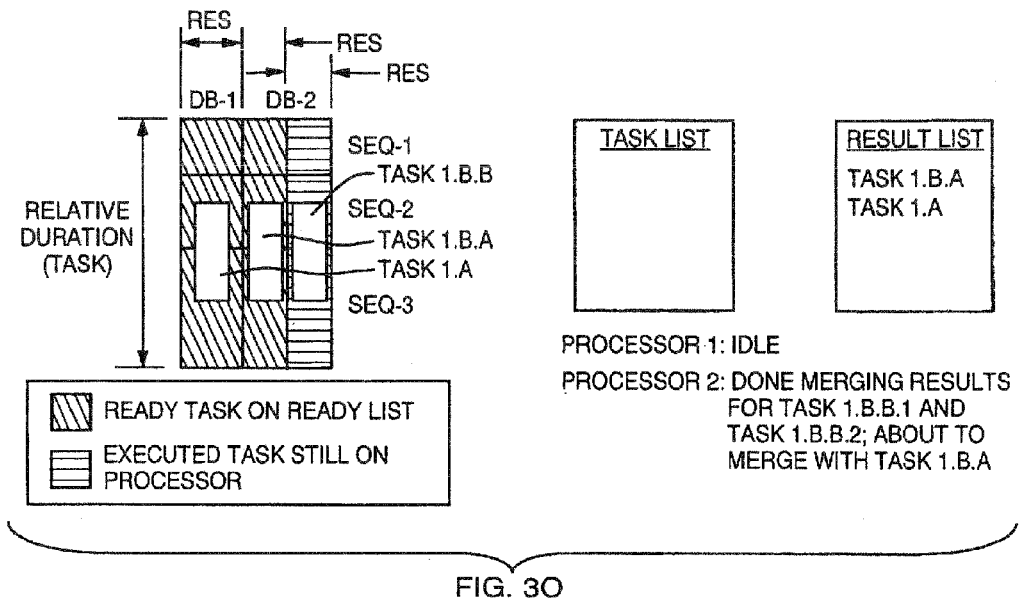
FIG. 3O illustrates a graphical representation of Processor 2 merging result for Task 1.B.B.1 with result for Buddy Task 1.B.B.2, thereby computing result for Parent Task 1.B.B. (Box E).
Figure 3P:
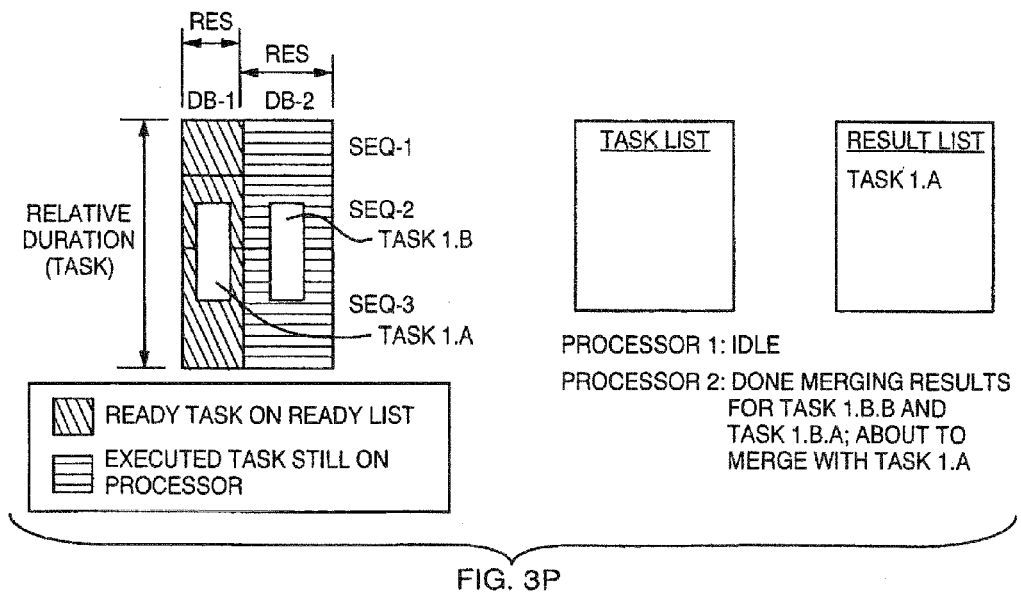
FIG. 3P illustrates a graphical representation of when Task 1.B.B.'s Buddy Task 1.B.A. is READY, Processor 2 mergers result for Task 1.B.B. with result for Buddy Task 1.B.A., thereby computing result for Parent Task 1.B (Box E).
Figure 3Q:
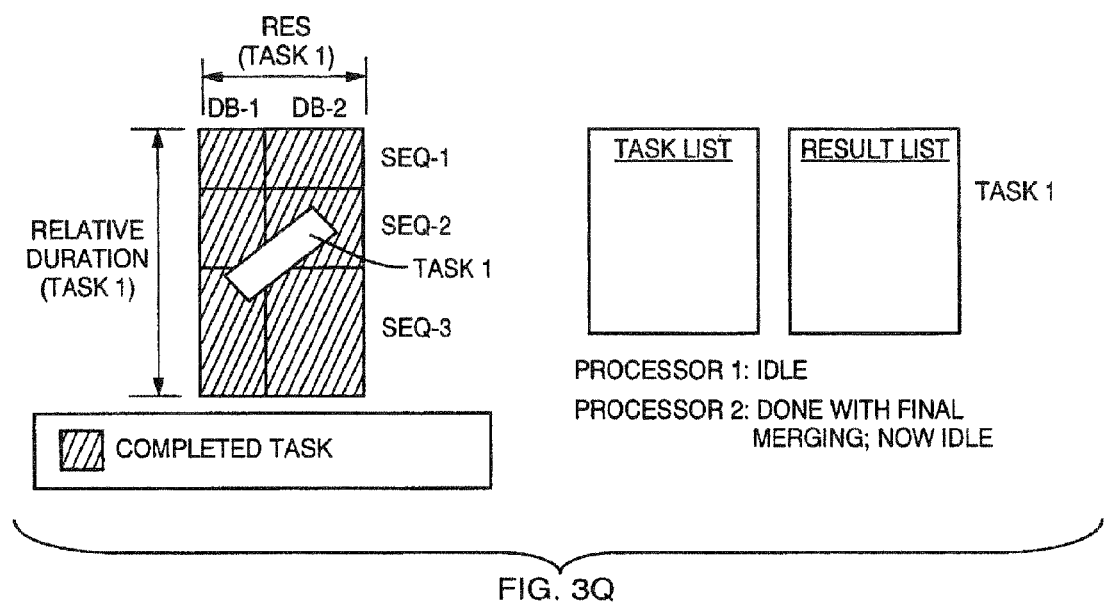
Figure 4:
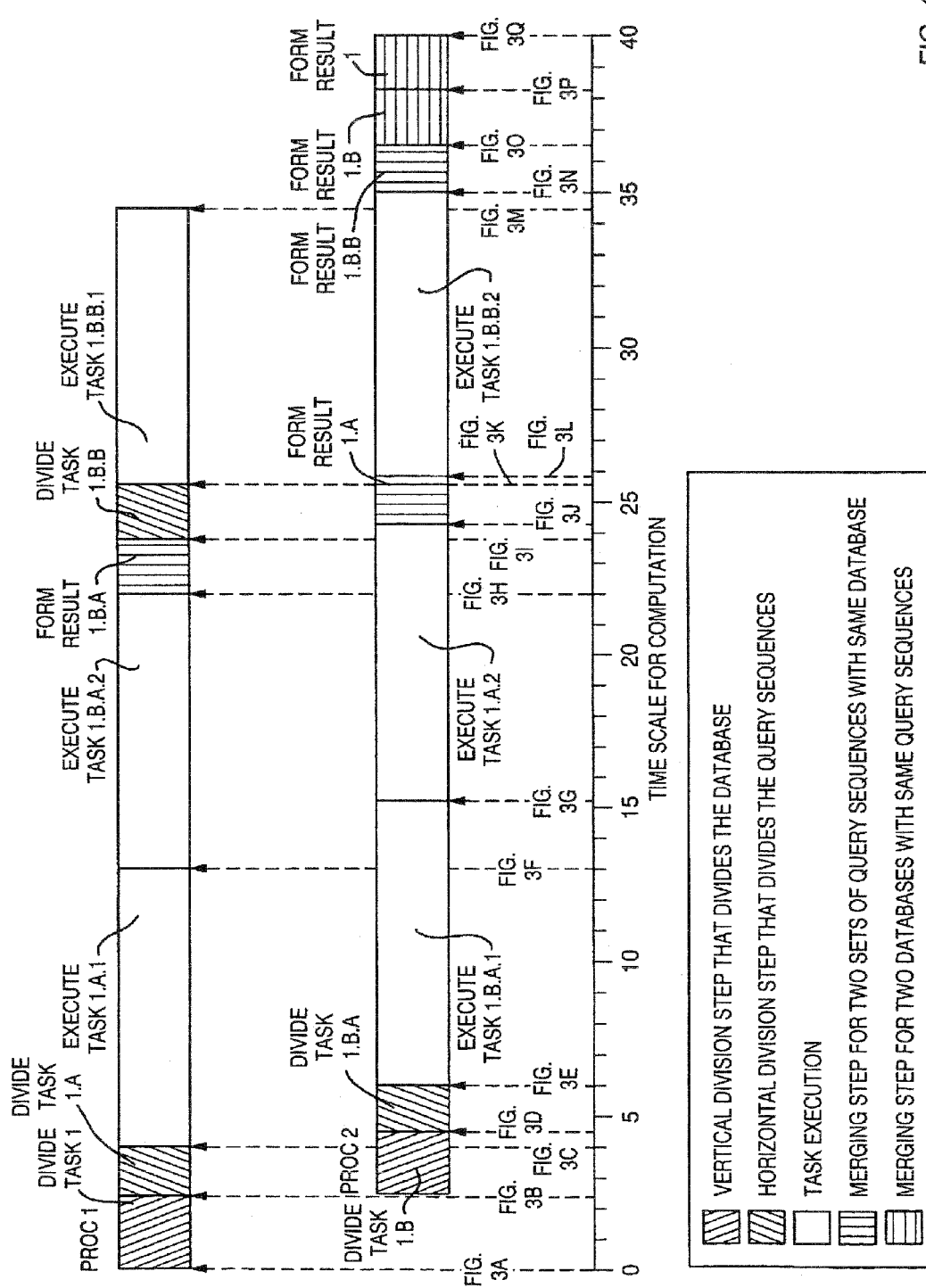
FIG. 4 is a timeline that corresponds to the examples of FIGS. 3A through 3Q.

(5) FIGS. 3O, 3P and 3Q illustrate the case of repeated hierarchical merges that eventually lead to the final result for the entire searching task.

FIG. 4 contains timelines that illustrate the activities carried out on each of two processors during application of the method of the invention to compute the result of the entire searching task as illustrated in FIGS. 3A through 3Q. The markings for each activity are described below. In this figure, the fill pattern for each activity reflects the type of activity. The time scale does not represent actual time, but is intended to portray possible relative times at which various activities might take place. The time scale is consistent with the details of FIGS. 3A through 3Q and with a possible operation of actual computer software implementing the method. The timelines are correlated with FIGS. 3A through 3Q.

Figure 5:
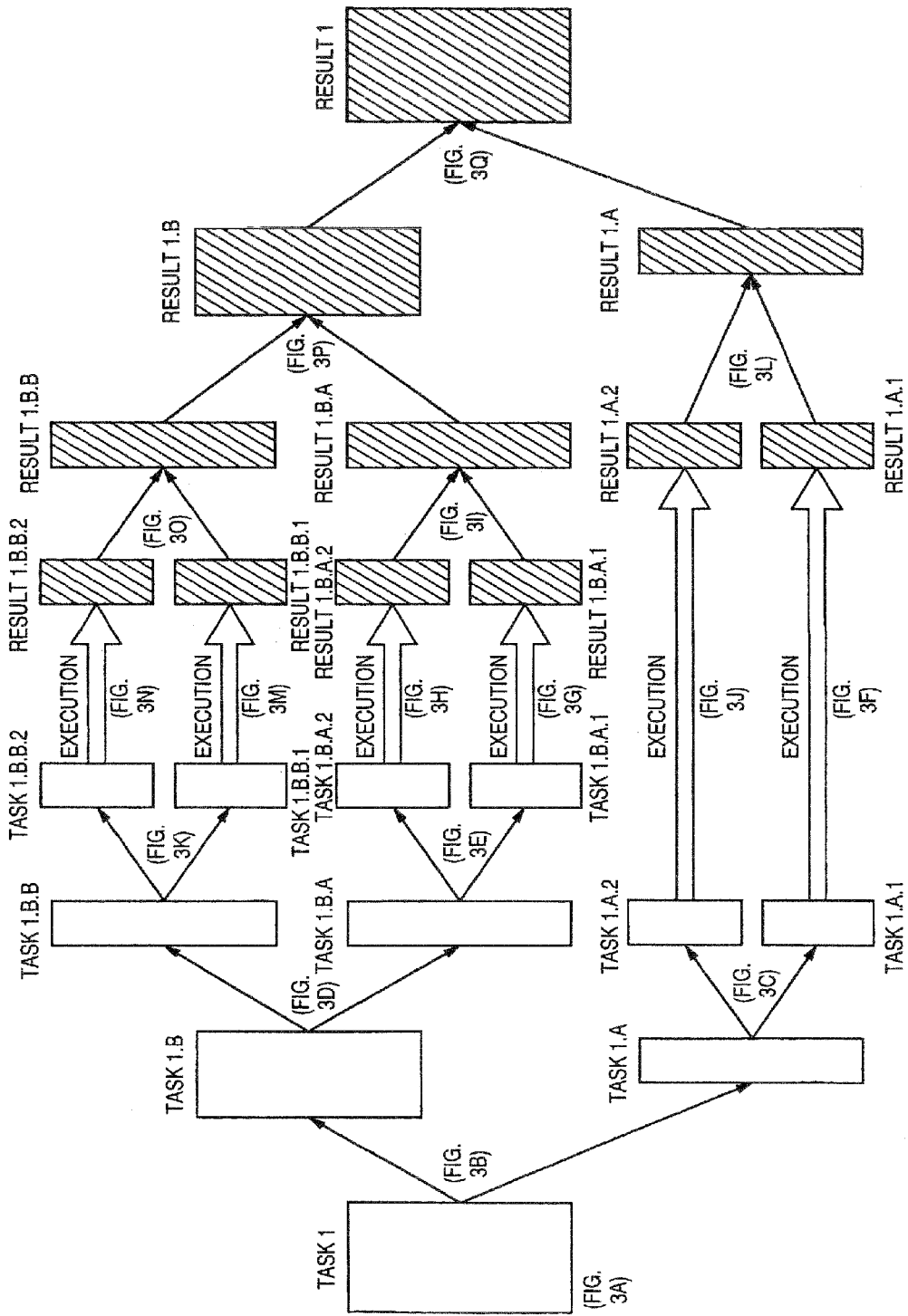
FIG. 5 is a graphical representation of the task division and result merging operations for the example of FIGS. 3A through 3Q.
Figure 6A:
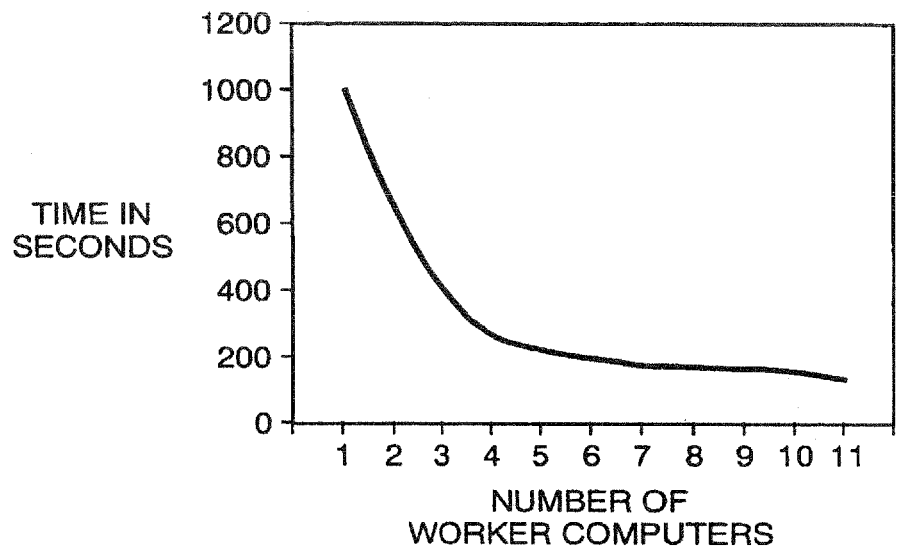
FIGS. 6A and 6B contain graphical comparisons of the performance of the sequence comparison method of the invention running on between 2 and 11 computers, with the performance of the NCBI BLAST program running on a single computer of the same type.
Figure 6B:
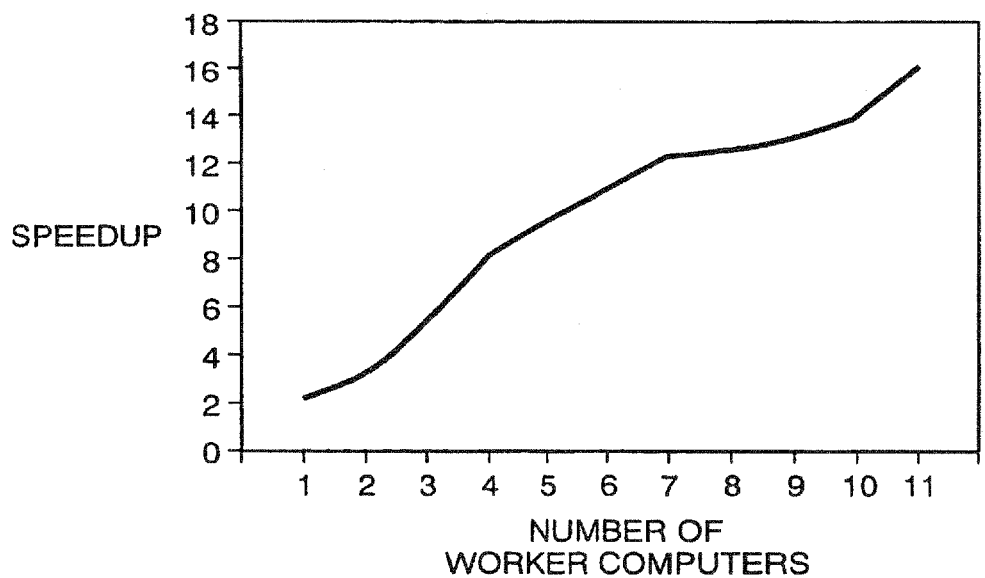

To complete the picture of the example of FIG. 3A through 3Q, FIG. 5 illustrates the task division and result merging operations using a binary tree representation. In FIG. 5, each division of a searching task into two smaller searching tasks is represented by a single white rectangle (representing the searching task to be divided) containing two outward-pointing arrows, each of which leads to a smaller white rectangle representing one of the two smaller searching tasks. The parenthesized letters refer to FIGS. 3A through 3Q. Task names also refer to the names used in FIGS. 3A through 3Q. Analogously, the creation of a unified result for a Parent Task by merging the computed results of two Buddy Tasks is represented by two gray rectangles (the Buddy tasks) connected by outward-pointing arrows to a single larger gray rectangle (the Parent task). As with the other figures, FIG. 5 contains lettered markings to correlate it with the subfigures of FIGS. 3A through 3Q.

B. Example 2

The example shown here provides a simple demonstration of the performance achievable with the invention. The example search task is specified as follows:

Query Sequences: 50 Expressed Sequence Tags (ESTs) totaling 18,500 DNA bases;

Databases: Three separate databases downloaded from NCBI as follows:

| NCBI Database | Sequences | DNA Bases (Approx.) |
|---|---|---|
| *Drosophila* | 1,170 | 123 million |
| GSS Division of GENBANK | Approx. 1.27 million | 651 million |
| *E-coli* | 400 | 4.6 million |

The benchmark example was run on a group of IBM Netfinity PCs, each containing a single 500-Megahertz Pentium III processor, 512 Kilobytes of cache memory, and 256 Megabytes of main memory. The PCs were connected on a switched 100 Megabit Ethernet network. All searches were made using the blastn variant of BLAST using the default set of BLAST parameters. The baseline BLAST was performed using the command:

blastall-d "ecoli.nt gss drosophila"-p blastn which required a time of 2131.8 seconds on one computer.

The table below shows the timing results obtained with varying numbers of worker computers. The "Speedup" is calculated as the ratio between the baseline time and the time using the method with the specified number of worker computers. Since the results clear show that the speedup using n worker computers may be greater than n, these results demonstrate the possibility of superlinear speedup with the method of the invention.

| Worker Computers | Time (seconds) | Speedup |
|---|---|---|
| 1 | 1011.0 | 2.11 |
| 2 | 646.0 | 3.30 |
| 3 | 393.0 | 5.42 |
| 4 | 259.5 | 8.22 |
| 5 | 218.0 | 9.78 |
| 6 | 191.7 | 11.12 |
| 7 | 171.0 | 12.47 |
| 8 | 167.3 | 12.74 |
| 9 | 161.0 | 13.24 |
| 10 | 151.0 | 14.12 |
| 11 | 130.0 | 16.40 |

The times and speedup values are plotted in FIGS. 6(*a*) and 6(*b*). Although the present invention has been described in detail with reference to the example above, it is understood that various modifications can be made without departing from the spirit of the invention. Accordingly, the invention is limited only by the following claims. All cited patents, patent applications, and publications referred to in this application are herein incorporated by reference in their entirety.

The invention claimed is:

1. A method, comprising:
configuring a computing device to:
partition a plurality of queries into subsets of queries and at least one database into subdatabases;
designate searching tasks by associating each of the subsets of queries with one or more of the subdatabases;
assign at least one searching task to at least one of a plurality of computing devices operating in parallel;
designate two or more subtasks as related tasks on a virtual shared memory bulletin board;
cause execution of the at least one searching task using the at least one of the plurality of computing devices; and
cause generation of a search result responsive to the execution of the at least one searching task.

2. A device, comprising:
means for partitioning a plurality of queries into subsets of queries and for partitioning at least one database into one or more subdatabases;
means for designating searching tasks by associating each of the subsets of queries with the one or more of the subdatabases;
means for assigning at least one searching task to one of a plurality of computing devices operating in parallel;
means for designating two or more subtasks as related tasks on a virtual shared memory bulletin board;
means for causing the execution of the at least one searching task on the one of the plurality of computing devices operating in parallel; and
means for causing the generation of a search result responsive to the means for causing the execution of the at least one searching task.

3. A computer readable medium including instructions stored thereon that when executed by a processor result in:
partitioning a plurality of queries into subsets of queries and at least one database into subdatabases;
designating searching tasks by associating each of the subsets of queries with one or more of the subdatabases;
assigning at least one searching task to at least one computer of a group of computers operating in parallel;
designating two or more subtasks as related tasks on a virtual shared memory bulletin board;
executing the at least one searching task using the at least one computer of the group of computers operating in parallel; and
generating a search result responsive to the executing.

4. The computer readable medium of claim 3 comprising dividing the searching tasks into subtasks.

5. The computer readable medium of claim 3 where the partitioning occurs responsive to a processing capacity of each computer of the group of computers operating in parallel.

6. The computer readable medium of claim 3 where each computer of the group of computers assigns to itself one or more of the searching tasks.

7. The computer readable medium of claim 3 comprising searching the plurality of queries against two or more databases.

8. The computer readable medium of claim 3 comprising executing two or more searching tasks by another computer during the execution of the at least one searching task using the at least one computer of the group of computer operating in parallel.

9. The computer readable medium of claim 3 comprising assigning another searching task to the at least one computer during the execution of other tasks by other computers of the group of computers operating in parallel.

10. The computer readable medium of claim 3 comprising performing all of the searching tasks by the group of computers operating in parallel.

11. The computer readable medium of claim 3 where each computer of the group of computers is substantially similar.

12. The computer readable medium of claim 3 where at least two computers of the group of computers are different.

13. The computer readable medium of claim 3 where each computer of the group of computers includes a same operating system.

14. The computer readable medium of claim 3 where at least two computers of the group of computers include a different operating system.

15. The computer readable medium of claim 3 where failure of any one computer of the group of computers does not affect the search results.

16. The computer readable medium of claim 3 comprising including a numerical score with the search results that indicates a quantitative measure of a match between the query and the database.

17. The computer readable medium of claim 3 where generating the search results includes showing speedup.

18. The computer readable medium of claim 3 where the generating of the search results occurs at a single computer of the group of computers operating in parallel.

19. The computer readable medium of claim 3 where the generating of the search results occurs at two or more computers of the group of computers operating in parallel.

20. The computer readable medium of claim 3 where the generating of the search results includes interleaving the search results responsive to a numerical score.

21. The computer readable medium of claim 3 comprising representing a search by a rectangular array in which each search task is assigned to one computer of the group of computers operating in parallel and is represented by adjacent rectangles in the array.

22. The computer readable medium of claim 21
where each column of the array represents at least one of the subdatabases; and
where each row represents one or more queries.

23. The computer readable medium of claim 22 where a width of at least one column of the array corresponds to a group of one or more subdatabases that can be substantially simultaneously stored in a memory in the at least one computer operating in parallel.

24. A system comprising:
at least one database; and
a plurality of computers operating in parallel, each computer including a processor that operates to:
partition a plurality of queries into a set of smaller subsets of queries;
partition the at least one database into a set of smaller subdatabases;
designates searching tasks to be performed by associating each of said subsets of queries with one or more of said subdatabases;
divide at least one of the searching tasks into two or more smaller searching tasks;
designate the two or more smaller tasks as related tasks on a virtual shared memory bulletin board;
execute at least some of the searching tasks responsive to getting assigned the at least some of the searching tasks;
collect search results from the executed searching tasks; and
generate a search result from the executed searching tasks.

25. The system of claim 24 where each of the plurality of computers is substantially identical to each other.

26. The system of claim 24 where at least two of the plurality of computers are different from one another.

27. The system of claim 24 where the plurality of computers operates using a same operating system.

28. The system of claim 24 where at least two computers of the plurality of computers operate using a different operating system.

29. The system of claim 24 where each computer is configured to compensate for failure of other computers in the plurality of computers operating in parallel so as to not affect the search results.

30. The system of claim 24
where the at least one database includes a plurality of records; and
where the plurality of records are nucleic acid sequence records or amino acid sequence records.

31. The system of claim 24 where the at least one database includes a database from the National Center for Biotechnology Information (NCBI).

32. The system of claim 24 where the processor further operates to execute a BLAST algorithm.

33. The system of claim 24 where the processor further operates to generate a sequence alignment result.

34. The system of claim 24 where the processor further operates to report a raw score associated with the search results.

35. The system of claim 24 where the processor further operates to report an e-score associated with the search results.

36. The system of claim 35 where the processor further operates to normalize the e-score.

37. The system of claim 24 where the processor further operates to report a relevance ranked result list responsive to the normalized e-score.

38. The system of claim 24 where the processor further operates to interleave the search results on the basis of raw scores generated during execution of the at least some searching tasks.

39. An apparatus, comprising:
a memory bulletin board shared by one or more computers operating in parallel;
a processor configured to:
partition a plurality of queries into subsets of queries;
partition at least one database into one or more subdatabases;
designate searching tasks by associating each of the subsets of queries with the one or more of the subdatabases;
assign at least one searching task to at least one of the one or more computers operating in parallel;
designate two or more subtasks as related tasks on the memory bulletin board;
generate a search report responsive to the at least one computer executing the at least one searching task.

* * * * *

UNITED STATES PATENT AND TRADEMARK OFFICE
CERTIFICATE OF CORRECTION

PATENT NO. : 7,761,462 B2
APPLICATION NO. : 11/969878
DATED : July 20, 2010
INVENTOR(S) : Bjornson et al.

Page 1 of 1

It is certified that error appears in the above-identified patent and that said Letters Patent is hereby corrected as shown below:

On Title Page 2, item (56), under "Other Publications", Line 16, delete "Verison 6.2," and insert
-- Version 6.2, --.

Signed and Sealed this
Twenty-seventh Day of March, 2012

David J. Kappos
*Director of the United States Patent and Trademark Office*